(12) United States Patent
Moskowitz et al.

(10) Patent No.: US 10,238,505 B2
(45) Date of Patent: *Mar. 26, 2019

(54) BI-DIRECTIONAL FIXATING/LOCKING TRANSVERTEBRAL BODY SCREW/INTERVERTEBRAL CAGE STAND-ALONE CONSTRUCTS

(71) Applicant: Moskowitz Family LLC, Rockville, MD (US)

(72) Inventors: Nathan C. Moskowitz, Rockville, MD (US); Mosheh Moskowitz, Rockville, MD (US); Ahmnon D. Moskowitz, Rockville, MD (US); Pablo A. Valdivia Y. Alvarado, Cambridge, MA (US)

(73) Assignee: Moskowitz Family LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/678,401

(22) Filed: Aug. 16, 2017

(65) Prior Publication Data

US 2018/0014945 A1 Jan. 18, 2018

Related U.S. Application Data

(60) Continuation of application No. 13/401,829, filed on Feb. 21, 2012, now Pat. No. 9,744,052, which is a
(Continued)

(51) Int. Cl.
*A61B 17/80* (2006.01)
*A61B 17/86* (2006.01)
(Continued)

(52) U.S. Cl.
CPC .......... *A61F 2/447* (2013.01); *A61B 17/8042* (2013.01); *A61B 17/86* (2013.01);
(Continued)

(58) Field of Classification Search
CPC .... A61F 2/447; A61F 2/44; A61F 2002/2835; A61F 2002/30476; A61F 2002/30772;
(Continued)

(56) References Cited

U.S. PATENT DOCUMENTS 2,360,942 A 10/1944 Ellerstein
4,064,881 A 12/1977 Meredith
(Continued)

FOREIGN PATENT DOCUMENTS

| FR | 2727003 | 5/1996 |
|----|---------|--------|
| WO | 2004/093749 | 11/2004 |
| WO | 2006/091503 | 8/2006 |

OTHER PUBLICATIONS

Dieter Grob et al., "Clinical Experience With the Dynesys Semirigid Fixation System for the Lumbar Spine," Spine, vol. 30, No. 3, 2005, pp. 324-331.
(Continued)

*Primary Examiner* — Pedro Philogene
(74) *Attorney, Agent, or Firm* — Fish & Richardson P.C.

(57) ABSTRACT

A bi-directional fixating transvertebral (BDFT) screw/cage apparatus is provided. The BDFT apparatus includes an intervertebral cage including a plurality of internal angled screw guides, a plurality of screw members, and a cage indentation adjacent to the screw guides that independently or supplemented by other screw locking mechanisms prevents the screw members from pulling out of the internal angled screw guides. The internal angled screw guides orient a first screw member superiorly and a second screw member inferiorly. The intervertebral cage is adapted for posterior lumbar intervertebral placement, anterior lumbar intervertebral placement, anterio-lateral thoracic intervertebral placement, or anterior cervical intervertebral placement.

20 Claims, 25 Drawing Sheets

Related U.S. Application Data continuation-in-part of application No. 13/103,994, filed on May 9, 2011, now Pat. No. 9,603,713, which is a division of application No. 12/054,335, filed on Mar. 24, 2008, now Pat. No. 7,972,363, which is a continuation-in-part of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279, application No. 15/678,401, which is a continuation of application No. 13/401,829, filed on Feb. 21, 2012, now Pat. No. 9,744,052, which is a continuation-in-part of application No. 13/084,543, filed on Apr. 11, 2011, now Pat. No. 8,353,913, which is a division of application No. 11/842,855, filed on Aug. 21, 2007, now Pat. No. 7,942,903, application No. 15/678,401, which is a continuation of application No. 13/401,829, filed on Feb. 21, 2012, now Pat. No. 9,744,052.

(60) Provisional application No. 61/451,582, filed on Mar. 10, 2011, provisional application No. 61/451,579, filed on Mar. 10, 2011, provisional application No. 61/445,034, filed on Feb. 21, 2011, provisional application No. 60/670,231, filed on Apr. 12, 2005.

(51) Int. Cl.
*A61B 17/92* (2006.01)
*A61F 2/30* (2006.01)
*A61F 2/44* (2006.01)
*A61F 2/28* (2006.01)

(52) U.S. Cl.
CPC . *A61B 2017/922* (2013.01); *A61F 2002/2835* (2013.01); *A61F 2002/30476* (2013.01); *A61F 2002/30772* (2013.01); *A61F 2002/30787* (2013.01); *A61F 2002/448* (2013.01); *A61F 2220/0025* (2013.01)

(58) Field of Classification Search
CPC ...... A61F 2002/30787; A61F 2002/448; A61F 2220/0025; A61B 17/8042; A61B 17/86; A61B 2017/922
USPC ......... 623/17.11–17.16; 606/96, 99, 104, 98, 606/87
See application file for complete search history.

(56) References Cited

U.S. PATENT DOCUMENTS

| | | | |
|---|---|---|---|
| 4,554,914 | A | 11/1985 | Kapp et al. |
| 4,599,086 | A | 7/1986 | Doty |
| 4,636,217 | A | 1/1987 | Ogilvie et al. |
| 4,904,261 | A | 2/1990 | Dove et al. |
| 4,960,420 | A | 10/1990 | Goble et al. |
| 4,997,432 | A | 3/1991 | Keller |
| 5,005,749 | A | 4/1991 | Aranyi |
| 5,062,850 | A | 11/1991 | MacMillan et al. |
| 5,123,926 | A | 6/1992 | Pisharodi |
| 5,290,312 | A | 3/1994 | Kojimoto et al. |
| 5,405,391 | A | 4/1995 | Henderson et al. |
| 5,413,583 | A | 5/1995 | Wohlers |
| 5,454,819 | A | 10/1995 | Knoepfler |
| 5,514,180 | A | 5/1996 | Heggeness et al. |
| 5,660,188 | A | 8/1997 | Groiso |
| 5,667,472 | A | 9/1997 | Finn et al. |
| 5,713,912 | A | 2/1998 | Porter |
| 5,782,832 | A | 7/1998 | Larsen et al. |
| 5,865,848 | A | 2/1999 | Baker |
| 5,888,223 | A | 3/1999 | Bray, Jr. |
| 5,916,224 | A | 6/1999 | Esplin |
| 5,951,574 | A | 9/1999 | Stefanchik et al. |
| 5,960,522 | A | 10/1999 | Boe |
| 5,968,054 | A | 10/1999 | Yeatts et al. |
| 5,976,136 | A | 11/1999 | Bailey et al. |
| 6,126,689 | A | 10/2000 | Brett |
| 6,224,602 | B1 | 5/2001 | Hayes |
| 6,235,034 | B1 | 5/2001 | Bray |
| 6,322,562 | B1 | 11/2001 | Wolter |
| 6,342,074 | B1 | 1/2002 | Simpson |
| 6,368,350 | B1 | 4/2002 | Erickson et al. |
| 6,375,682 | B1 | 4/2002 | Fleischmann et al. |
| 6,419,704 | B1 | 7/2002 | Ferree |
| 6,432,106 | B1 | 8/2002 | Fraser |
| 6,454,807 | B1 | 9/2002 | Jackson |
| 6,458,159 | B1 | 10/2002 | Thalgott |
| 6,527,804 | B1 | 3/2003 | Gauchet et al. |
| 6,533,818 | B1 | 3/2003 | Weber et al. |
| 6,558,423 | B1 | 5/2003 | Michelson |
| 6,572,653 | B1 | 6/2003 | Simonson |
| 6,579,318 | B2 | 6/2003 | Varga et al. |
| 6,582,468 | B1 | 6/2003 | Gauchet |
| 6,613,055 | B2 | 9/2003 | Di Emidio |
| 6,629,998 | B1 | 10/2003 | Lin |
| 6,641,614 | B1 | 11/2003 | Wagner et al. |
| 6,655,243 | B2 | 12/2003 | Anderson et al. |
| 6,716,247 | B2 | 4/2004 | Michelson |
| 6,719,794 | B2 | 4/2004 | Gerber |
| 6,723,126 | B1 | 4/2004 | Berry |
| 6,733,532 | B1 | 5/2004 | Gauchet et al. |
| 6,764,491 | B2 | 7/2004 | Frey et al. |
| 6,770,094 | B2 | 8/2004 | Fehling et al. |
| 6,824,564 | B2 | 11/2004 | Crozet |
| 6,852,117 | B2 | 2/2005 | Orlowski |
| 6,890,355 | B2 | 5/2005 | Michelson |
| 6,904,308 | B2 | 6/2005 | Frisch et al. |
| 6,953,477 | B2 | 10/2005 | Berry |
| 6,955,671 | B2 | 10/2005 | Uchikubo |
| 6,962,606 | B2 | 11/2005 | Michelson |
| 6,972,019 | B2 | 12/2005 | Michelson |
| 6,974,480 | B2 | 12/2005 | Messerli et al. |
| 7,030,904 | B2 | 4/2006 | Adair et al. |
| 7,033,394 | B2 | 4/2006 | Michelson |
| 7,037,258 | B2 | 5/2006 | Chatenever et al. |
| 7,077,864 | B2 | 7/2006 | Byrd et al. |
| 7,097,615 | B2 | 8/2006 | Banik et al. |
| 7,135,043 | B2 | 11/2006 | Nakahara et al. |
| 7,211,112 | B2 | 5/2007 | Baynham et al. |
| 7,232,464 | B2 | 6/2007 | Mathieu et al. |
| 7,238,203 | B2 | 7/2007 | Bagga et al. |
| 7,326,248 | B2 | 2/2008 | Michelson |
| 7,442,209 | B2 | 10/2008 | Michelson |
| 7,442,299 | B2 | 10/2008 | Lee et al. |
| 7,615,059 | B2 | 11/2009 | Watschke et al. |
| 7,618,456 | B2 | 11/2009 | Mathieu et al. |
| 7,628,816 | B2 | 12/2009 | Magerl et al. |
| 7,704,279 | B2 | 4/2010 | Moskowitz et al. |
| 7,727,246 | B2 | 6/2010 | Sixto et al. |
| 7,776,047 | B2 * | 8/2010 | Fanger ............... A61B 17/1757 606/96 |
| 7,776,093 | B2 | 8/2010 | Wolek et al. |
| 7,803,162 | B2 | 9/2010 | Marnay et al. |
| 7,846,207 | B2 | 12/2010 | Lechmann et al. |
| 7,862,616 | B2 | 1/2011 | Lechmann et al. |
| 7,875,076 | B2 | 1/2011 | Mathieu et al. |
| 7,887,591 | B2 | 2/2011 | Aebi et al. |
| 7,942,903 | B2 | 5/2011 | Moskowitz et al. |
| 7,959,675 | B2 | 6/2011 | Gately |
| 7,972,363 | B2 * | 7/2011 | Moskowitz ........ A61B 17/0642 606/246 |
| 7,985,255 | B2 | 7/2011 | Bray et al. |
| 8,029,512 | B2 | 10/2011 | Paltzer |
| 8,034,060 | B2 | 10/2011 | Keren et al. |
| 8,105,367 | B2 | 1/2012 | Austin et al. |
| 8,114,162 | B1 | 2/2012 | Bradley |
| 8,137,405 | B2 | 3/2012 | Kostuik et al. |
| 8,167,949 | B2 | 5/2012 | Tyber et al. |

(56) References Cited

U.S. PATENT DOCUMENTS

| | | | |
|---|---|---|---|
| 8,268,000 B2 | 9/2012 | Waugh et al. | |
| 8,273,127 B2* | 9/2012 | Jones | A61F 2/4455 623/17.16 |
| 8,328,872 B2 | 12/2012 | Duffield et al. | |
| 8,353,913 B2 | 1/2013 | Moskowitz et al. | |
| 8,403,986 B2 | 3/2013 | Michelson | |
| 8,414,651 B2 | 4/2013 | Tyber et al. | |
| 8,419,797 B2 | 4/2013 | Biedermann et al. | |
| 8,425,607 B2* | 4/2013 | Waugh | A61F 2/447 606/246 |
| 8,540,774 B2 | 9/2013 | Kueenzi et al. | |
| 8,613,761 B2 | 12/2013 | Lindemann et al. | |
| 8,728,165 B2 | 5/2014 | Parry et al. | |
| 8,790,405 B2 | 7/2014 | Biedermann et al. | |
| 9,005,293 B2 | 4/2015 | Moskowitz | |
| 9,744,052 B2* | 8/2017 | Moskowitz | A61F 2/447 |
| 2002/0068977 A1 | 6/2002 | Jackson | |
| 2002/0143338 A1 | 10/2002 | Orbay et al. | |
| 2003/0130737 A1 | 7/2003 | McGahan et al. | |
| 2004/0088054 A1 | 5/2004 | Berry | |
| 2004/0177531 A1 | 9/2004 | Dibenedetto et al. | |
| 2004/0186569 A1 | 9/2004 | Berry | |
| 2004/0193272 A1 | 9/2004 | Zubok et al. | |
| 2004/0220571 A1 | 11/2004 | Assaker et al. | |
| 2004/0254644 A1 | 12/2004 | Taylor | |
| 2005/0027362 A1 | 2/2005 | Williams et al. | |
| 2005/0049590 A1 | 3/2005 | Alleyne et al. | |
| 2005/0177235 A1 | 8/2005 | Baynham et al. | |
| 2005/0216084 A1 | 9/2005 | Fleischmann | |
| 2005/0256576 A1 | 11/2005 | Moskowitz et al. | |
| 2005/0261769 A1 | 11/2005 | Moskowitz et al. | |
| 2005/0273170 A1 | 12/2005 | Navarro et al. | |
| 2005/0278026 A1 | 12/2005 | Gordon et al. | |
| 2006/0155285 A1* | 7/2006 | Anderson | A61B 17/8042 606/70 |
| 2006/0241621 A1 | 10/2006 | Moskowitz et al. | |
| 2007/0049943 A1 | 3/2007 | Moskowitz et al. | |
| 2007/0167678 A1 | 7/2007 | Moskowitz et al. | |
| 2007/0198089 A1 | 8/2007 | Moskowitz et al. | |
| 2007/0213820 A1 | 9/2007 | Magerl et al. | |
| 2007/0250167 A1 | 10/2007 | Bray et al. | |
| 2007/0250172 A1 | 10/2007 | Moskowitz et al. | |
| 2007/0276498 A1 | 11/2007 | Aebi et al. | |
| 2008/0033440 A1 | 2/2008 | Moskowitz et al. | |
| 2008/0177307 A1 | 7/2008 | Moskowitz et al. | |
| 2008/0183293 A1 | 7/2008 | Parry et al. | |
| 2008/0249569 A1 | 10/2008 | Waugh et al. | |
| 2008/0249575 A1 | 10/2008 | Waugh et al. | |
| 2008/0249625 A1 | 10/2008 | Waugh et al. | |
| 2008/0281424 A1 | 11/2008 | Parry et al. | |
| 2008/0281425 A1 | 11/2008 | Thalgott et al. | |
| 2009/0030520 A1 | 1/2009 | Biedermann et al. | |
| 2009/0080997 A1 | 3/2009 | Johnson | |
| 2009/0105830 A1 | 4/2009 | Jones et al. | |
| 2009/0105831 A1 | 4/2009 | Jones | |
| 2009/0112271 A1 | 4/2009 | Moskowitz et al. | |
| 2009/0182430 A1 | 7/2009 | Tyber | |
| 2009/0187218 A1 | 7/2009 | Schaffhausen | |
| 2009/0210062 A1 | 8/2009 | Thalgott et al. | |
| 2009/0224023 A1 | 9/2009 | Moskowitz et al. | |
| 2009/0234455 A1 | 9/2009 | Moskowitz et al. | |
| 2010/0145460 A1 | 6/2010 | McDonough et al. | |
| 2010/0305704 A1 | 12/2010 | Messerli et al. | |
| 2010/0324606 A1 | 12/2010 | Moskowitz et al. | |
| 2011/0125269 A1 | 5/2011 | Moskowitz et al. | |
| 2011/0137349 A1 | 6/2011 | Moskowitz et al. | |
| 2011/0178600 A1 | 7/2011 | Moskowitz et al. | |
| 2011/0208312 A1 | 8/2011 | Moskowitz et al. | |
| 2011/0288646 A1 | 11/2011 | Moskowitz et al. | |
| 2011/0295327 A1 | 12/2011 | Moskowitz et al. | |
| 2011/0295371 A1 | 12/2011 | Moskowitz et al. | |
| 2011/0307011 A1 | 12/2011 | Moskowitz et al. | |
| 2011/0319935 A1 | 12/2011 | Moskowitz et al. | |
| 2012/0010714 A1 | 1/2012 | Moskowitz et al. | |
| 2012/0271423 A1 | 10/2012 | Wallenstein et al. | |
| 2012/0277870 A1 | 11/2012 | Wolters et al. | |
| 2012/0323330 A1 | 12/2012 | Kueenzi et al. | |
| 2012/0330419 A1 | 12/2012 | Moskowitz et al. | |
| 2013/0018468 A1 | 1/2013 | Moskowitz et al. | |
| 2013/0018469 A1 | 1/2013 | Moskowitz et al. | |
| 2013/0018470 A1 | 1/2013 | Moskowitz et al. | |
| 2013/0023991 A1 | 1/2013 | Moskowitz et al. | |
| 2013/0023992 A1 | 1/2013 | Moskowitz et al. | |
| 2013/0053962 A1 | 2/2013 | Moskowitz et al. | |
| 2013/0060339 A1 | 3/2013 | Duffield et al. | |
| 2013/0073044 A1 | 3/2013 | Gamache | |
| 2013/0173002 A1 | 7/2013 | Moskowitz et al. | |
| 2013/0282017 A1 | 10/2013 | Moskowitz et al. | |
| 2014/0249629 A1 | 9/2014 | Moskowitz et al. | |
| 2015/0025637 A1 | 1/2015 | Moskowitz et al. | |
| 2015/0105824 A1 | 4/2015 | Moskowitz et al. | |
| 2015/0148847 A1 | 5/2015 | Moskowitz et al. | |
| 2016/0374830 A1 | 12/2016 | Moskowitz et al. | |
| 2017/0252178 A1 | 9/2017 | Moskowitz et al. | |

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.

E.K. Wai et al.. "Disk Replacement Arthroplasties: Can the Success of Hip and Knee Replacements be Repeated in the Spine?." Seminars in Spine Surgery, vol. 15, No. 4 Dec. 2003, pp. 473-482.

Richard D. Guyer et al., "Intervertebral Disc Prostheses," Spine Journal, vol. 28, No. 15S, Supp. to Aug. 1, 2003, pp. S15-S23.

International Search Report (ISR) and Written Opinion of the International Searching Authority, dated Dec. 3, 2007, International Application No. PCT/US 07/05005.

International Search Report (ISR) and Written Opinion of the International Searching Authority, dated Jul. 9, 2008, International Application No. PCT/US2007/021013.

International Search Report (ISR) and Written Opinion of the International Searching Authority, dated May 21, 2008, International Application No. PCT/US2007/021015.

* cited by examiner

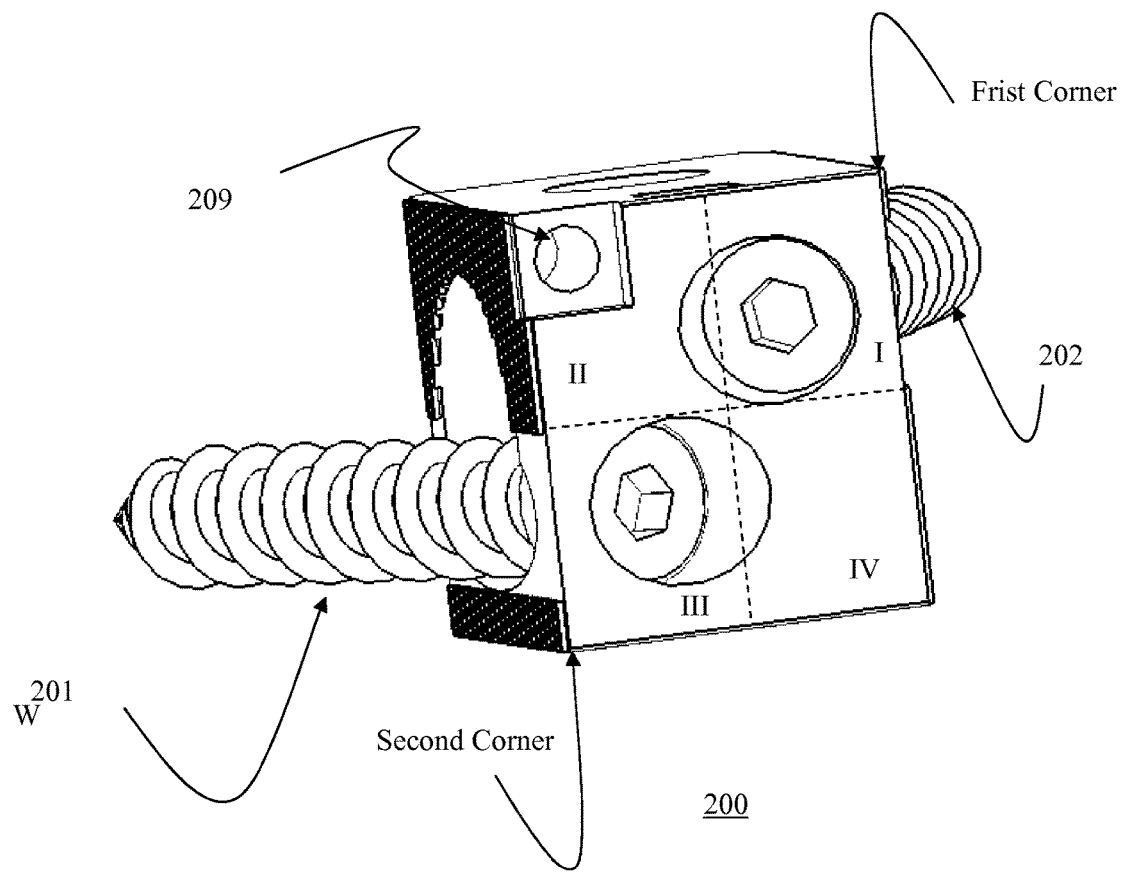
Fig. 7C(ii)

BI-DIRECTIONAL FIXATING/LOCKING TRANSVERTEBRAL BODY SCREW/INTERVERTEBRAL CAGE STAND-ALONE CONSTRUCTS

This application is a Continuation-In-Part Application, for which priority is claimed under 35 U.S.C. § 120, of copending U.S. patent application Ser. No. 13/103,994, filed on May 9, 2011, which is a Divisional of U.S. patent application Ser. No. 12/054,335, filed on Mar. 24, 2008 (now U.S. Pat. No. 7,972,363 B2, issued on Jul. 5, 2011), which is a Continuation-In-Part of application Ser. No. 11/842,855, filed on Aug. 21, 2007 (now U.S. Pat. No. 7,942,903, issued May 17, 2011), which is a Continuation-In-Part of application Ser. No. 11/536,815, filed on Sep. 29, 2006 (now U.S. Pat. No. 7,846,188 B2, issued Dec. 7, 2010), which is a Continuation-In-Part of application Ser. No. 11/208,644, filed on Aug. 23, 2005 (now U.S. Pat. No. 7,704,279 issued on Apr. 27, 2010), the entire contents of all of the above identified patent applications are hereby incorporated by reference in their entirety and for which priority of each of the above-identified applications is claimed under 35 U.S.C. § 120.

This application also is a Continuation-In-Part Application, for which priority is claimed under 35 U.S.C. § 120, of application Ser. No. 13/084,543, filed on Apr. 11, 2011, which is a Divisional of application Ser. No. 11/842,855, filed on Aug. 21, 2007 (now U.S. Pat. No. 7,942,903, issued May 17, 2011), which is a Continuation-In-Part of application Ser. No. 11/536,815, filed on Sep. 29, 2006 (now U.S. Pat. No. 7,846,188 B2, issued Dec. 7, 2010), which is a Continuation-In-Part of application Ser. No. 11/208,644, filed on Aug. 23, 2005 (now U.S. Pat. No. 7,704,279 issued on Apr. 27, 2010), the entire contents of all of the above identified patent applications are hereby incorporated by reference in their entirety and for which priority of each of the above-identified applications is claimed under 35 U.S.C. § 120.

This application also claims priority under 35 U.S.C. § 119(e) of U.S. Provisional Application No. 61/451,582, filed on Mar. 10, 2011, U.S. Provisional Application No. 61/451,579, filed on Mar. 10, 2011, and U.S. Provisional Application No. 61/445,034, filed on Feb. 21, 2011, the entire contents of all of the above identified patent applications are hereby incorporated by reference in their entirety.

U.S. patent application Ser. No. 13/084,543, filed on Apr. 11, 2011, Ser. No. 11/842,855, filed on Aug. 21, 2007, Ser. No. 11/536,815, filed on Sep. 29, 2006, and Ser. No. 11/208,644, filed on Aug. 23, 2005, each claim the benefit of priority under 35 U.S.C. § 119(e) of U.S. Provisional Application No. 60/670,231, filed on Apr. 12, 2005, and this application hereby incorporates the claim of priority to this provisional application under 35 U.S.C. § 119(e) from the aforementioned intermediate applications (for which priority of each intermediate application is claimed under 35 U.S.C. § 120); and the entire contents of all of the above identified patent applications are hereby incorporated by reference in their entirety.

FIELD OF DISCLOSURE

The present invention relates to a unique universal bi-directional screw (BDS) system, and in particular its application to the spine, also referred to as bi-directional fixating transvertebral (BDFT) screw/cage constructs which can be used as stand-alone intervertebral devices which combine the dual functions of an intervertebral spacer that can be filled with bone fusion material(s), as well as a bi-directional transvertebral bone fixating/fusion screw apparatus. In the posterior lumbosacral and thoracic spine, intervertebral cage/BDFT screw constructs can be used as stand-alone devices obviating the need for pedicle screw fixation in many but not all cases. In the anterior cervical, thoracic and lumbosacral spine, intervertebral cage/BDFT screw constructs can be used as stand-alone devices obviating the need for anterior or lateral (thoracic and lumbosacral) spinal plating, and/or supplemental posterior pedicle screw fixation.

BACKGROUND

The history and evolution of instrumented spinal fusion in the entire human spine has been reviewed in related application Ser. No. 12/054,335, filed on Mar. 24, 2008, Ser. No. 13/084,543, filed on Apr. 11, 2011, Ser. No. 11/842,855, filed on Aug. 21, 2007, Ser. No. 11/536,815, filed on Sep. 29, 2006, and Ser. No. 11/208,644, filed on Aug. 23, 2005, the contents of which are hereby incorporated by reference in their entirety. Conventionally, the majority of posterior cervical and almost all posterior thoracic and lumbosacral fusion surgical techniques are typically supplemented with pedicle screw placement. Conventionally, the majority of anterior cervical spinal fusions, and many anterio-lateral thoracic, and anterior or anterio-lateral lumbosacral fusions are supplemented with anterior or anterior-lateral spinal plating, and very often, in particular in the thoracic and lumbosacral spine, are supplemented with posterior pedicle screw instrumentation.

Complications of pedicle screw placement in cervical, thoracic and lumbosacral spine include duration of procedure, significant tissue dissection and muscle retraction, misplaced screws with neural and/or vascular injury, excessive blood loss, need for transfusions, prolonged recovery, incomplete return to work, and excessive rigidity leading to adjacent segmental disease requiring further fusions and re-operations. Recent advances in pedicle screw fixation including minimally invasive, and stereotactic CT image-guided technology, and the development of flexible rods, imperfectly address some but not all of these issues.

Complications of anterior plating in the cervical spine include potential plate, and/or screw esophageal compression, and misplaced screws leading to neurovascular injury. Complications of anterior, or anterior-lateral plating in the anterior lumbar spine include potential devastating injury to the major vessels due to chronic vascular erosion of the major vessels, or acute vascular injuries due to partial or complete plate and/or screw back out. Furthermore, for re-do surgeries, plate removal can be arduous, with potential complications of prolonged esophageal retraction, vascular injury and screw breakage. Recent advances including diminishing the plate width and/or profile, and absorbable plates, imperfectly address some but not all of these issues.

Complications of all conventional spinal anterior interverterbral device constructs include the potential for extrusion of these conventional constructs in the absence of plating. Hence, these conventional constructs are supplemented with anterior plating to prevent extrusion. Complications of posterior lumbosacral intervertebral device construct in the presence or absence of supplemental pedicle screw fixation include device extrusion, and potential nerve root and/or vascular injuries.

SUMMARY

Herein described are a plurality of device embodiments which combine in a single stand-alone construct the dual functions of: a) an intervertebral cage spacer which can be filled with bone fusion material maintaining disc height, and, b) a bi-directional fixating/fusion transvertebral body screw apparatus. These embodiments are described for posterior and anterior lumbar (and anterio-lateral thoracic) intervertebral placement, and anterior cervical intervertebral placement. The present invention recognizes the aforementioned problems with prior art apparatus and solves these problems by, among other things, improving upon the designs illustrated in the aforementioned related applications. The present application provides an advanced and novel bi-directional fixating transvertebral (BDFT) screw/cage apparatus with a modified novel cage which has indentations on the upper aspect of the screw box adjacent to the internalized angled screw guide. These new indentations have three functions: 1) the indentations distribute physical forces more equally and evenly in the contact interface between screw and box, thereby enhancing the integrity and the strength of the cage itself upon screw insertion thereby diminishing the cage's possibility of it breaking or cracking, and 2) the indentations allow for the placement of screws with larger screw heads which further increases the strength of screw engagement, and 3) the indentations further diminish the possibility of screw back out acting as an independent or supplemental screw locking mechanisms. Although this cage indentation modification precludes the need for an additional screw locking mechanism, this cage is never the less compatible with and can be supplemented by any of our three previously described novel screw locking mechanisms detailed in the related copending applications identified above. This novel interbody cage is also compatible with any other screw locking mechanism. This cage indentation modification is capable of functioning as an independent screw-locking mechanism, which when supplemented with any of the described screw locking mechanisms of any of the related copending applications identified above, or with any other screw locking mechanism, further increases the strength of the cage, improves screw/cage engagement and further prevents screw back out. All these novel modifications combined further improve the probability of a solid fusion with the embodiments described herein.

The exemplary embodiments of a bi-directional fixating transvertebral (BDFT) screw/cage apparatus provide as strong or stronger segmental fusion as pedicle screws without the complications arising from pedicle screw placement, which include misplacement with potential nerve and/or vascular injury, violation of healthy facets, possible pedicle destruction, blood loss, and overly rigid fusions. By placing screws across the intervertebral space from vertebral body to vertebral body, engaging anterior and middle spinal columns and not the vertebral bodies via the transpedicular route thereby excluding the posterior spinal column, then healthy facet joints, if they exist, are preserved. Because the present invention accomplishes both anterior and middle column fusion, without rigidly fixating the posterior column, the present invention in essence creates a flexible fusion.

The present invention recognizes that the very advantage of transpedicular screws which facilitate a strong solid fusion by rigidly engaging all three spinal columns is the same mechanical mechanism whereby complete inflexibility of all columns is incurred thereby leading to increasing rostral and caudal segmental stress which can lead to an increased rate of re-operation.

Transvertebral fusion also may lead to far less muscle retraction, blood loss and significant reduction in operating room (O.R.) time. Thus, the complication of pedicle screw pull out, and hence high re-operation rate associated with the current embodiment of flexible fusion pedicle screws/rods is obviated. The lumbosacral intervertebral cage/BDFT screw constructs can be introduced via posterior, lateral, transforaminal or anterior interbody fusion approaches/surgical techniques. Although one can opt to supplement these constructs with transpedicular screws, there would be no absolute need for supplemental pedicle screw fixation with these operative techniques.

The anterior placement of a bi-directional fixating transvertebral (BDFT) screw/cage apparatus according to the embodiments of the present invention into the cervical and lumbar spine obviates the need for supplemental anterior cervical or anterior lumbar plating. The sole purpose of these plates is to prevent intervertebral device extrusion. This function is completely obviated and replaced by the dual functioning bi-directional fixating transvertebral (BDFT) screw/cage apparatus, according to the present invention. The embodiments provide important advantages of providing a significant savings in operative time, and reducing or preventing of injuries associated with plating, in particular esophageal, for example, large and small vessel injuries, and spinal cord nerve root injuries.

Because the embodiments of the bi-directional fixating transvertebral (BDFT) screw/cage apparatus engage a small percentage of the rostral and caudal vertebral body surface area, multi-level fusions can be performed with these devices.

Conventionally, failed anterior lumbar arthroplasties are salvaged by combined anterior and posterior fusions. Intervertebral cage/BDFT screw constructs may be utilized as a one-step salvage mechanism for failed/extruded anteriorly placed lumbar artificial discs obviating the need for supplemental posterior pedicle screws an/or anterior lumbar plating thereby significantly reducing and/or eliminating co-morbidities associated with these other salvage procedures.

Likewise, anterior cervical intervertebral cage/BDFT screw construct placement can be used to salvage failed anterior cervical arthroplasties, and re-do fusions without having to supplement with cervical anterior plates, thereby reducing the morbidity of this procedure.

In addition, if a patient develops a discogenic problem necessitating anterior cervical discectomy and fusion at a level above or below a previously fused and plated segment, the present invention reduces or eliminates the need to remove the prior plate in order to place a new superior plate, because the function of the plate is replaced by the dual functioning intervertebral cervical construct, thereby reducing the operating room time and surgical morbidity of this procedure.

Furthermore, because of the orientation and length of the BDFT screws within the intervertebral cage/BDFT constructs, multiple level fusions can be easily performed.

For example, an exemplary embodiment is directed to an intervertebral cage spacer and bi-directional fixating/fusion transvertebral body screw/cage apparatus. The apparatus includes an intervertebral cage for maintaining disc height. The intervertebral cage includes a first internal screw guide and a second internal screw guide adjacent to novel cage indentations which function as independent or supplemental screw locking mechanisms. The apparatus further includes a first screw member having a tapered end and a threaded body disposed within the intervertebral cage, a second screw member having a tapered end and a threaded body disposed within the intervertebral cage, and a first screw locking mechanism that prevents the first screw member and the second screw from pulling-out of the first internal screw guide and the second internal screw guide. Such a screw locking mechanism is described in an exemplary embodiment of the related copending applications identified above.

Another exemplary embodiment is directed to an integral intervertebral cage spacer and bi-directional fixating/fusion transvertebral body screw apparatus, including an intervertebral cage having a plurality of internal angled screw guides. The apparatus further includes a plurality of screw members having a tapered end and a threaded body disposed within the plurality of internal angled screw guides of the intervertebral cage, which are adjacent to novel cage indentations which function independently as a screw locking mechanisms or functions in tandem with a previously described screw locking mechanism preventing the plurality of screw members from pulling out of the plurality of internal angled screw guides.

Another exemplary embodiment is directed to a method of inserting a bi-directional fixating transvertebral (BDFT) screw/cage apparatus between a first vertebral body and a second vertebral body. The method includes measuring a dimension of a disc space between the first vertebral body and the second vertebral body, determining that the disc space is a posterior or lateral lumbar disc space, an anterior lumbar disc space, or an anterior cervical disc space, selecting an intervertebral cage based on the measured dimension of the disc space and based on the determination of the disc space being the posterior lumbar disc space, the lateral lumbar disc space, the anterior lumbar disc space, or the anterior cervical disc space, inserting the selected intervertebral cage into a midline of the disc space until the selected intervertebral cage is flush or countersunk relative to the first vertebral body and the second vertebral body, inserting a first screw member into a first internal screw guide of the selected intervertebral cage, inserting a second screw member into a second internal screw guide of the selected intervertebral cage, screwing the first screw member and the second screw member into the first vertebral body and the second vertebral body respectively, confirming a position and placement of the intervertebral cage relative to the first vertebral body and the second vertebral body, and locking the first screw member and the second screw member in a final position by embedding a portion of the first screw member and the second screw member into a previously described screw locking mechanism and into a novel surrounding cage indentation of the selected intervertebral cage. In the absence of any supplemental screw locking mechanism, the heads of the first and second screw members can directly engage the surface of the cage and the adjacent novel indentations directly. These indentations themselves function as independent or supplemental screw locking mechanisms.

BRIEF DESCRIPTION OF THE DRAWINGS

The accompanying drawings are presented to aid in the description of embodiments of the invention and are provided solely for illustration of the embodiments and not limitation thereof.

DETAILED DESCRIPTION OF THE EXEMPLARY EMBODIMENTS

Figure 1A:
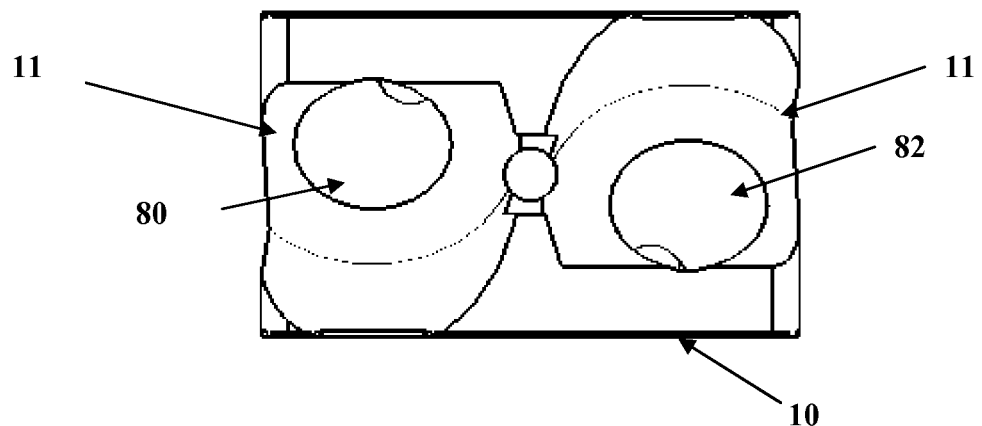
FIG. 1A illustrates a top view of an anterior cervical cage with novel indentations in a top surface according to an embodiment of the invention.

Aspects of the invention are disclosed in the following description and related drawings directed to specific embodiments of the invention. Alternate embodiments may be devised without departing from the scope of the invention. Additionally, well-known elements of the invention will not be described in detail or will be omitted so as not to obscure the relevant details of the invention.

The word "exemplary" is used herein to mean "serving as an example, instance, or illustration." Any embodiment described herein as "exemplary" is not necessarily to be construed as preferred or advantageous over other embodiments. Likewise, the term "embodiments of the invention" does not require that all embodiments of the invention include the discussed feature, advantage or mode of operation.

With reference to FIGS. 1A-7E, exemplary embodiments of the invention will now be described.

1. Exemplary Medical Device

Referring to FIGS. 1A-7E, the above described problems of the conventional art can be solved in the cervical, thoracic and lumbosacral spines by insertion of multiple embodiments of a bi-directional fixating transvertebral (BDFT) screw/cage apparatus into the denuded intervertebral disc space.

For example, FIGS. 1A-1C and 2A-2G illustrate three-dimensional views of an exemplary embodiment of an anterior cervical intervertebral cage/BDFT construct including an intervertebral cage 10 for maintaining disc height. The intervertebral cage 10 can include a first internal screw guide 80 and a second internal screw guide 82. A first screw member 30 having a tapered end and a threaded body and a second screw member 40 having a tapered end and a threaded body are disposed within the first internal screw guide 80 and the second internal screw guide 82 of the intervertebral cage 10.

Figure 1B:
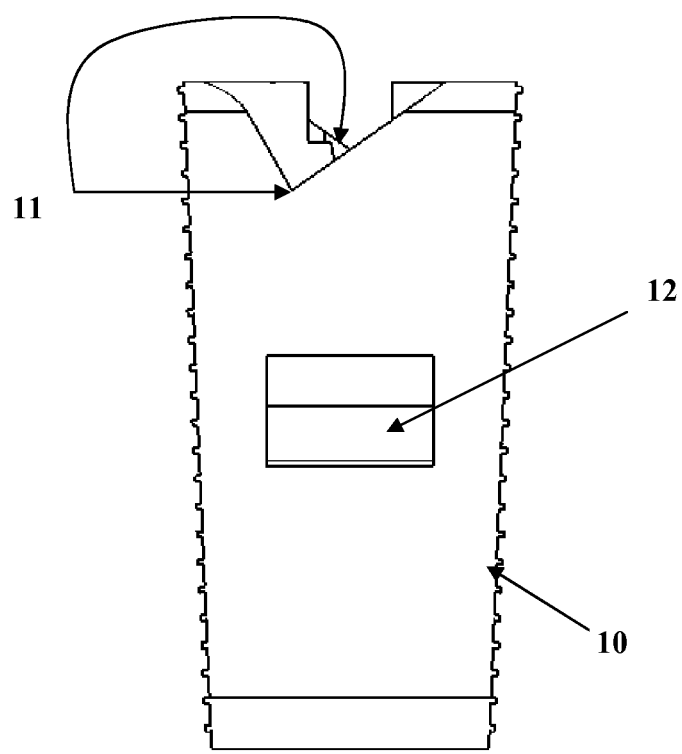
FIG. 1B illustrates a side (lateral) view of an anterior cervical cage with novel indentations in the top surface according to an embodiment of the invention.
Figure 1C:
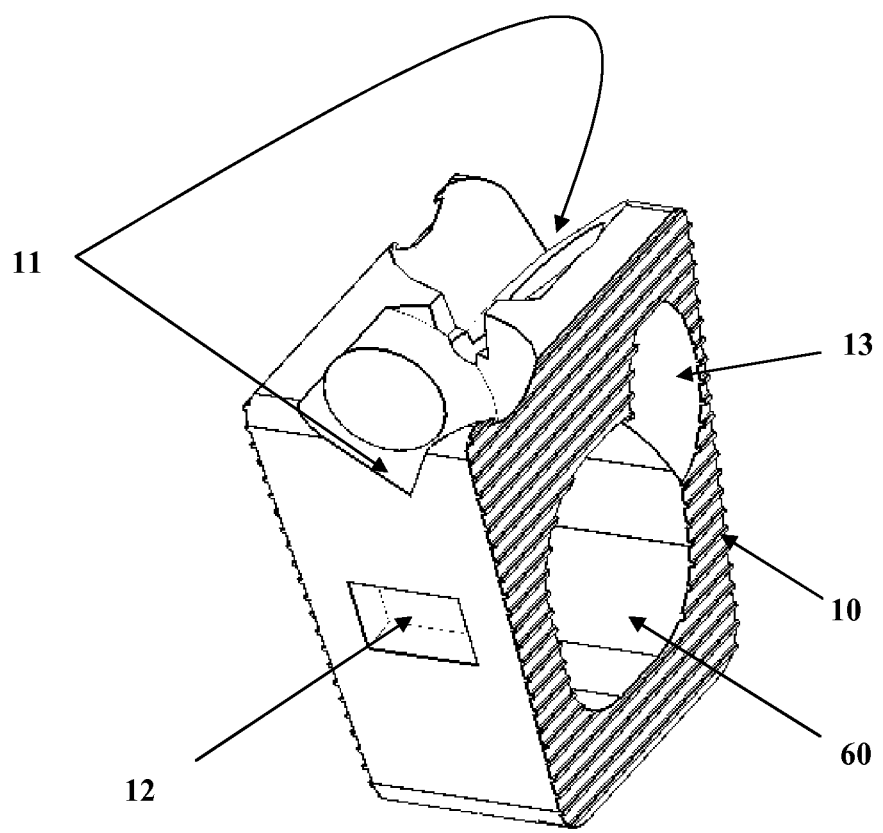
FIG. 1C illustrates a perspective (oblique) view of an anterior cervical cage with novel indentations in a top surface according to an embodiment of the invention.
Figure 2A:
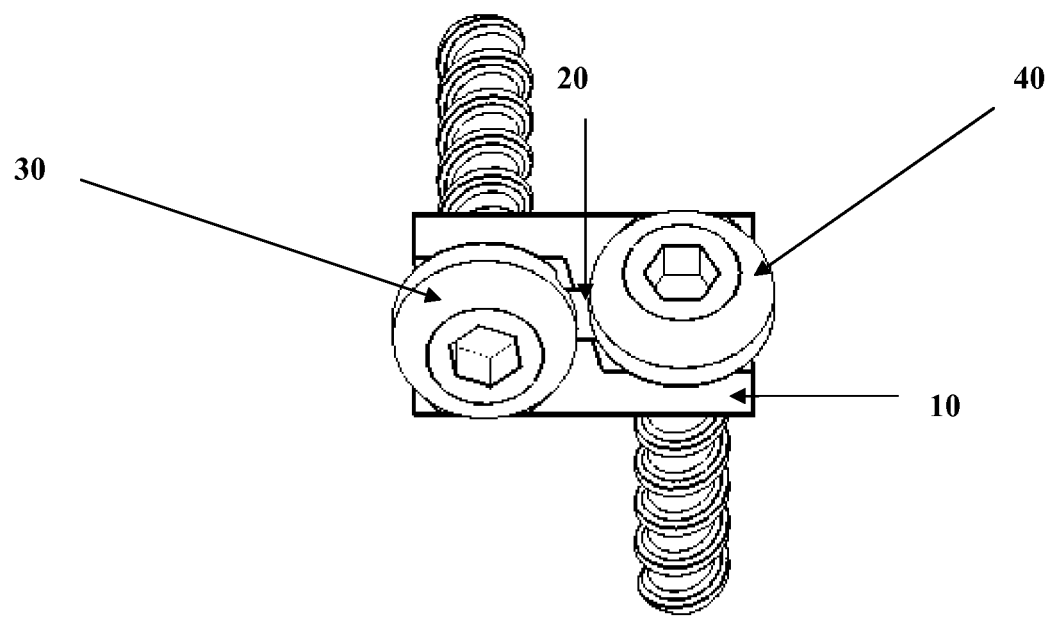
FIG. 2A illustrates a top view of an anterior cervical intervertebral cage/BDFT screw construct according to an embodiment of the invention.
Figure 2B:
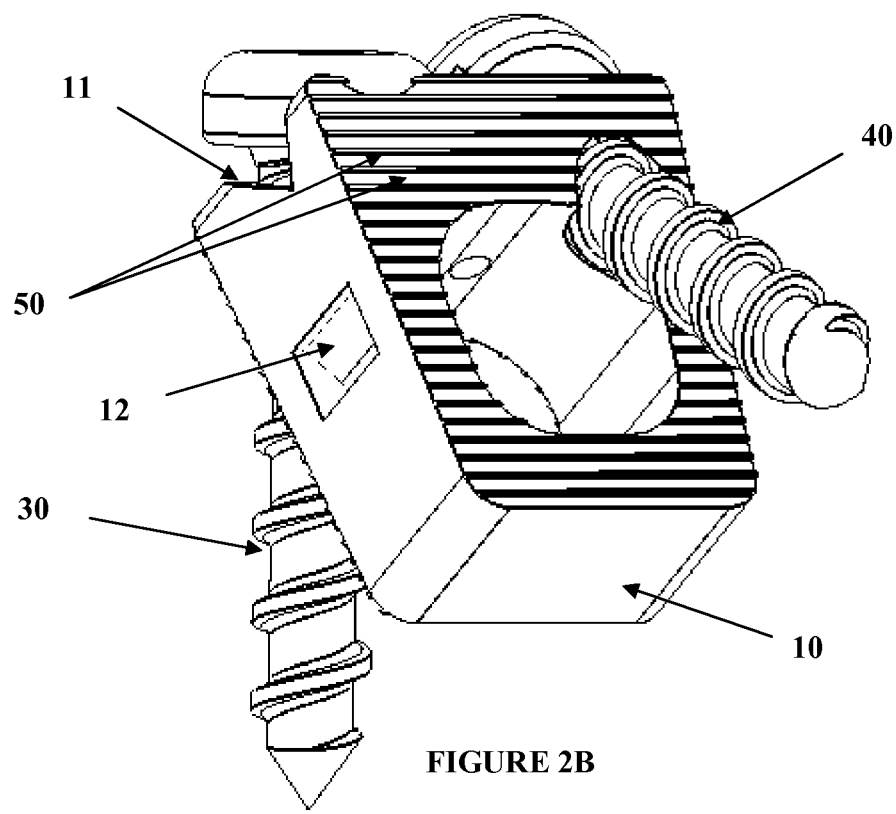
FIG. 2B illustrates a bottom, perspective (bottom isometric) view of an anterior cervical intervertebral cage/BDFT screw construct according to an embodiment of the invention.
Figure 2C:
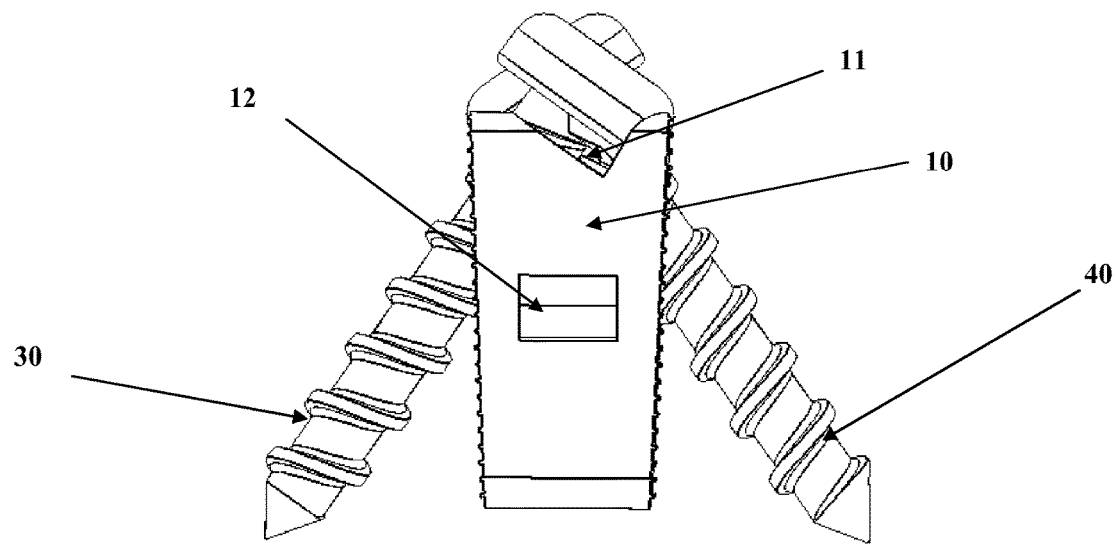
FIG. 2C illustrates a side view of an anterior cervical intervertebral cage/BDFT screw construct according to an embodiment of the invention.
Figure 2D:
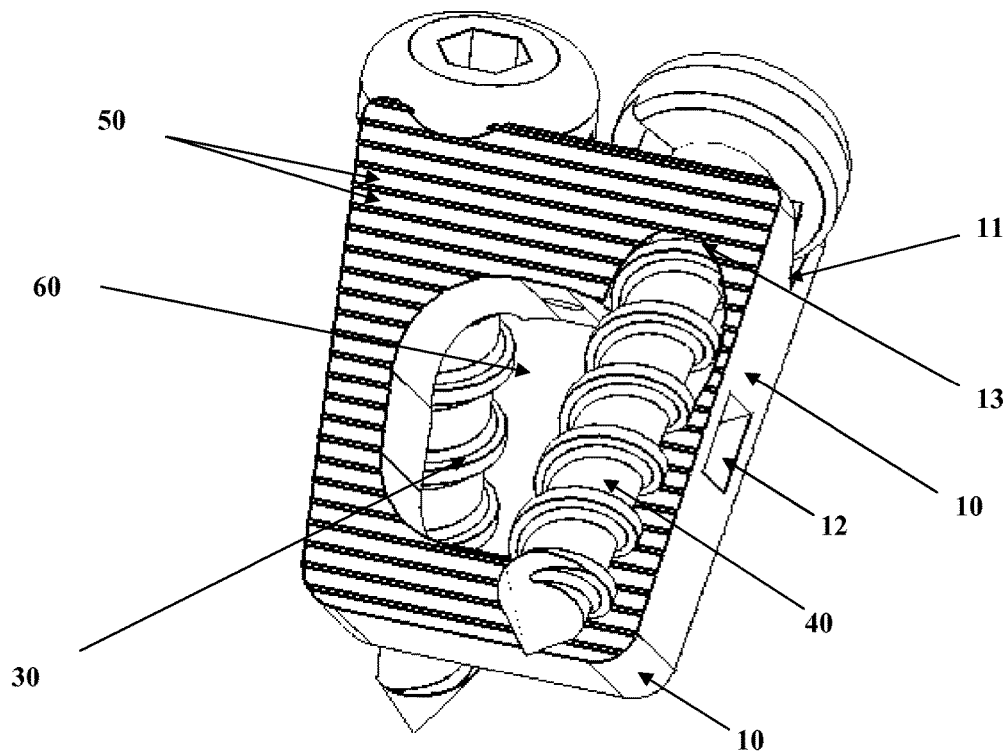
FIG. 2D illustrates bottom, perspective (bottom isometric) view of an anterior cervical intervertebral cage/BDFT screw construct according to an embodiment of the invention.
Figure 2E:
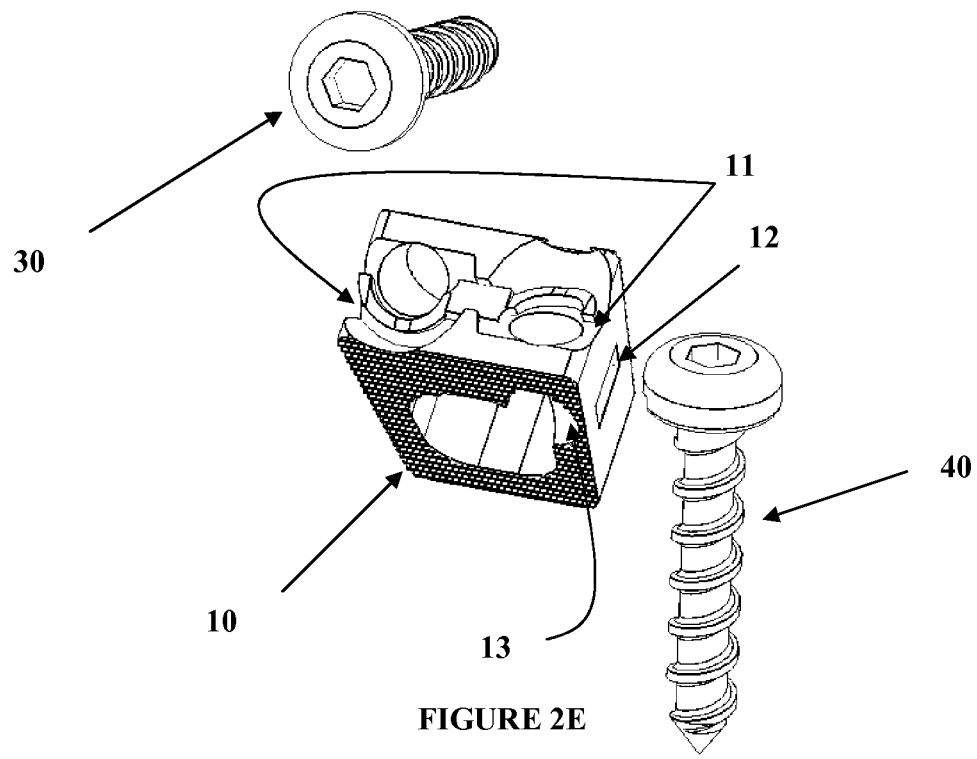
FIG. 2E illustrates a top, perspective, partially exploded (top isometric) view of an anterior cervical intervertebral cage/BDFT screw construct according to an embodiment of the invention.
Figure 2F:
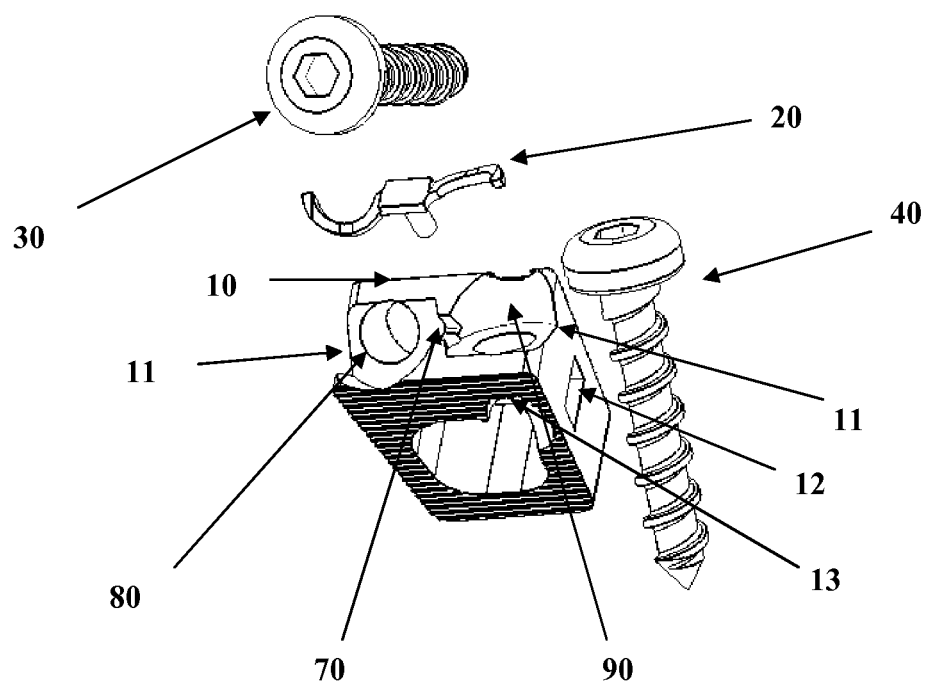
FIG. 2F illustrates a top, perspective, exploded view of an anterior cervical intervertebral cage/BDFT screw construct with internalized angled screw guides according to an embodiment of the invention.
Figure 2G:
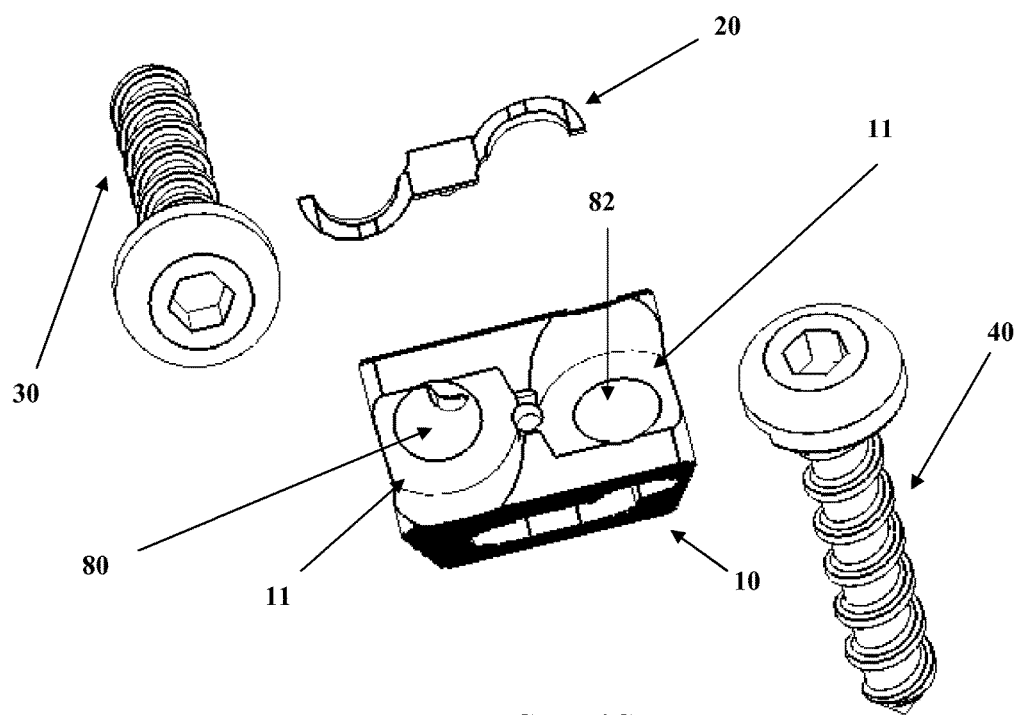
FIG. 2G illustrates a top, perspective, exploded view of an anterior cervical intervertebral cage/BDFT screw construct with internalized angled screw guides according to an embodiment of the invention.

In this exemplary embodiment, a top portion of a cage 10 can include indentations 11 adjacent to the internalized screw guides 80, 82, for example, to distribute physical forces surrounding the screw/cage interface and/or strengthen the cage 10 (FIGS. 1A-1C). The indentations 11 can be formed only in the top surface of the cage 10, or in the top surface and an edge of the top surface of the cage 10, as illustrated in the exemplary embodiment. The indentations 11 can function as independent or supplemental screw locking mechanisms. The cage 10 can be supplemented by, and is compatible with, any screw locking mechanism, for example screw locking member 20, that prevents the first screw member 30 and/or the second screw member 40 from pulling-out of the first internal screw guide 80 and the second internal screw guide 82. The indentations 11 can be, for example, triangular, which may distribute the force acting on the cage 10, thereby improving or increasing the strength of the cage 10. As shown in the exemplary embodiments, the cage 10 can include an opening or slot between the guides 80, 82 for receiving a separate or secondary locking mechanism, as described in more detail below.

The cage 10 also can include indentations 12 on the sides of the cage 10 for insertion of the prongs of an insertion device. In another embodiment, the sides of the cage 10 can be elliptically contoured when viewed from the side (e.g., side view of FIG. 2C) to fit into the bi-concave cervical disc space. The embodiment includes two screws 30, 40. A first screw 30 is oriented rostrally (superiorly) and a second screw 40 is oriented caudally (inferiorly). The cage 10 can include a cavity 60 for bone product placement.

The cage 10 includes two built in internalized screw/drill guides 80, 82, one for each screw 30, 40, which orient the screws 30, 40 bi-directionally in opposite directions. In an embodiment, the cage includes at least one screw guide 80 or 82 having a predetermined trajectory (e.g., preferably having a 25 degree angulation) that may make placement of all screws equally facile, more amenable to multi-level placement, and may diminish the need for external drill guides. In other embodiments, the cage includes at least two screw guides 80, 82 having a predetermined trajectory (e.g., preferably having a 25 degree angulation) that may make placement of all screws equally facile, more amenable to multi-level placement, and may diminish the need for external drill guides.

In other embodiments, the cage can include a screw guide 80, 82 having another predetermined trajectory, such as an angulation of substantially 25 degrees (e.g., an angulation ranging from 20 degrees to 30 degrees). In other embodiments, the cage can include a screw guide 80, 82 having another predetermined trajectory, such as an angulation ranging from 20 degrees to 25 degrees, an angulation ranging from 25 degrees to 30 degrees, an angulation ranging from 25 degrees to 35 degrees, an angulation ranging from 25 degrees to 35 degrees, an angulation ranging from 20 degrees to 40 degrees, etc. The embodiments of the cage can include one or more screw/drill guides 80, 82 having different angles and/or different positions within the cage.

A screw guide tunnel exit 13 is adjacent to the bone cavity, for example, as illustrated in FIGS. 1C, 2B, 2D, 2E, and 2F. One of ordinary skill in the art will recognize that the internalized screw/drill guides 80, 82 can have different degrees of angulation and/or different positions within the cage 10. The built in tunnels of the screw guides 80, 82 provide an important advantage of ensuring that only one prescribed angled trajectory is possible for transvertebral screw placement. Embodiments of the intervertebral cages can be designed with internalized screw/drill guides 80, 82 with different angles and/or different positions within the cage. The angle and size of the screws 30, 40 make them amenable to single or multi-level placement. The superior and inferior surfaces or edges of the lumbar cage can include ridges 50 or the like to facilitate integration and fusion with superior and inferior vertebral bodies.

The embodiment also can include a screw locking mechanism 20 which can be, for example, press-fit to the top of the cage 10. The top of the cage 10 can include a perforation 90 and/or an indentation 70 for each locking mechanism 20. Each locking mechanism 20 also can be designed to rest and be press-fit into the superior surface of the in-built self drilling screw guides 80, 82. The screw locking mechanism 20 can be manufactured from a variety of materials, such as titanium. When the screws 30, 40 are turned into the screw locking mechanism 20, the screws 30, 40 lock by mechanically indenting the screw locking mechanism 20, thereby preventing back-out or pull-out. The locking mechanism 20 can be reused for a limited number of cycles. In the absence of this locking mechanism, the screws 30, 40 can be screwed directly into the cage 10 with its surrounding indentations 11 which function as independent or supplemental screw locking mechanisms. The indentations 11 are an evolutionary advance and improvement compared to the apparatus illustrated in the aforementioned related applications. The novel embodiments of the present invention are quite unique and different from all other conventional screw locking mechanisms. No other conventional anterior cervical intervertebral cage/BDFT screw constructs are known.

Figure 3A:
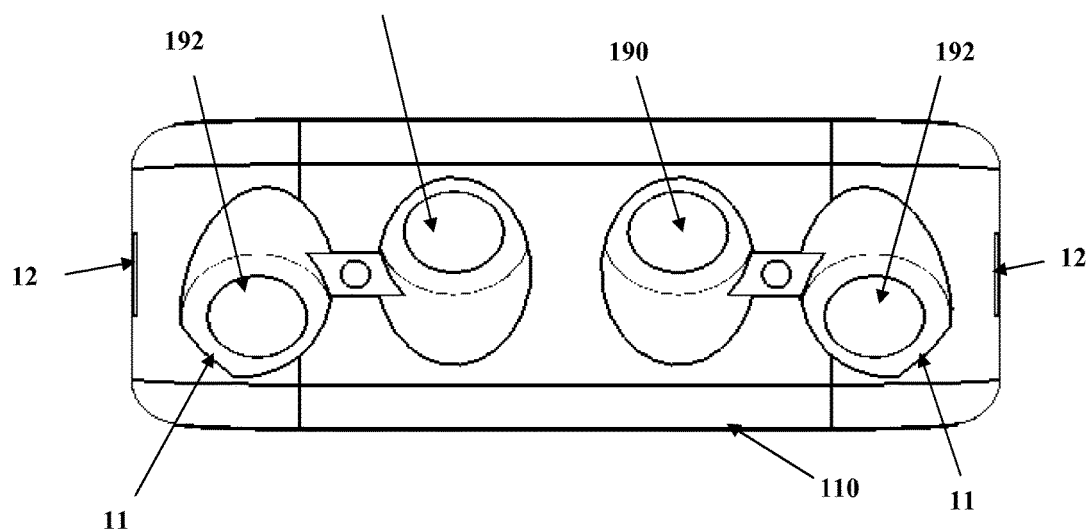
FIG. 3A illustrates a top view of an anterior Lumbar intervertebral cage with novel indentations according to an embodiment of the invention.
Figure 3B:
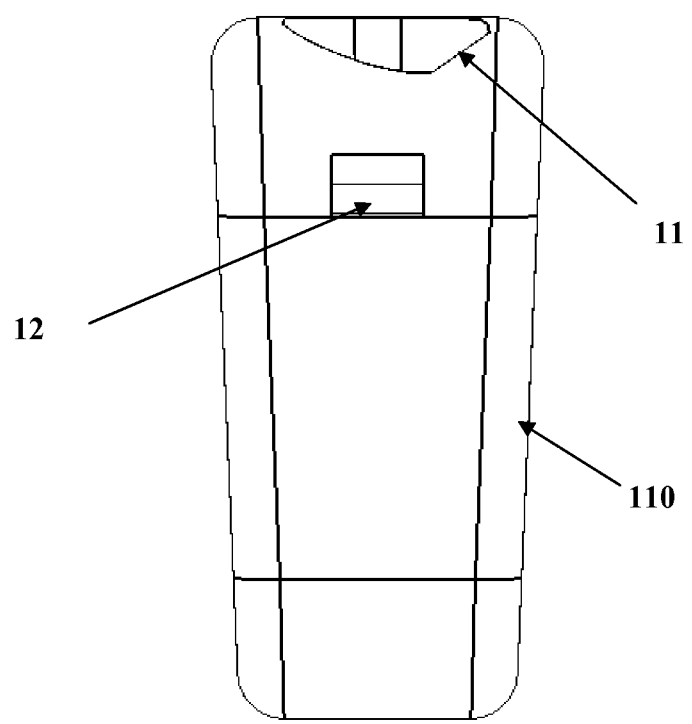
FIG. 3B illustrates a side view of an anterior Lumbar intervertebral cage with novel indentations according to an embodiment of the invention.
Figure 3C:
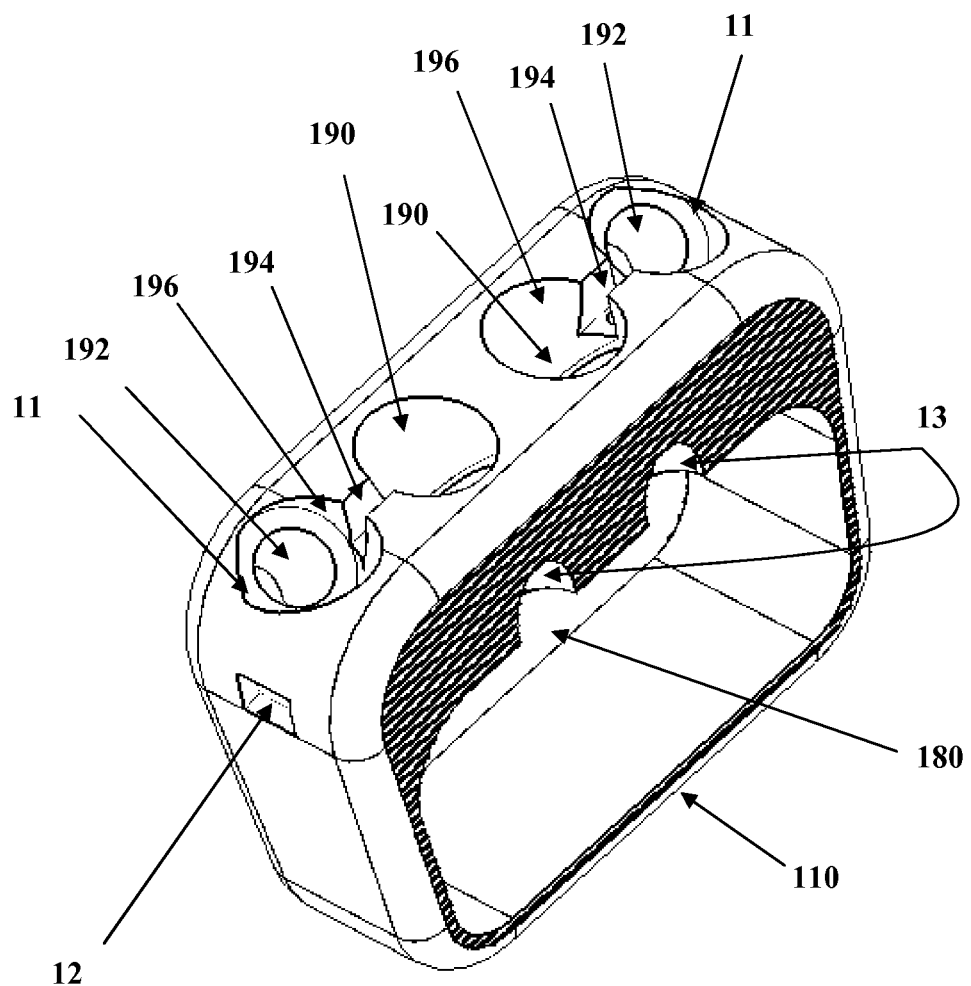
FIG. 3C illustrates a top, perspective view of an anterior Lumbar intervertebral cage with novel indentations according to an embodiment of the invention.
Figure 4A:
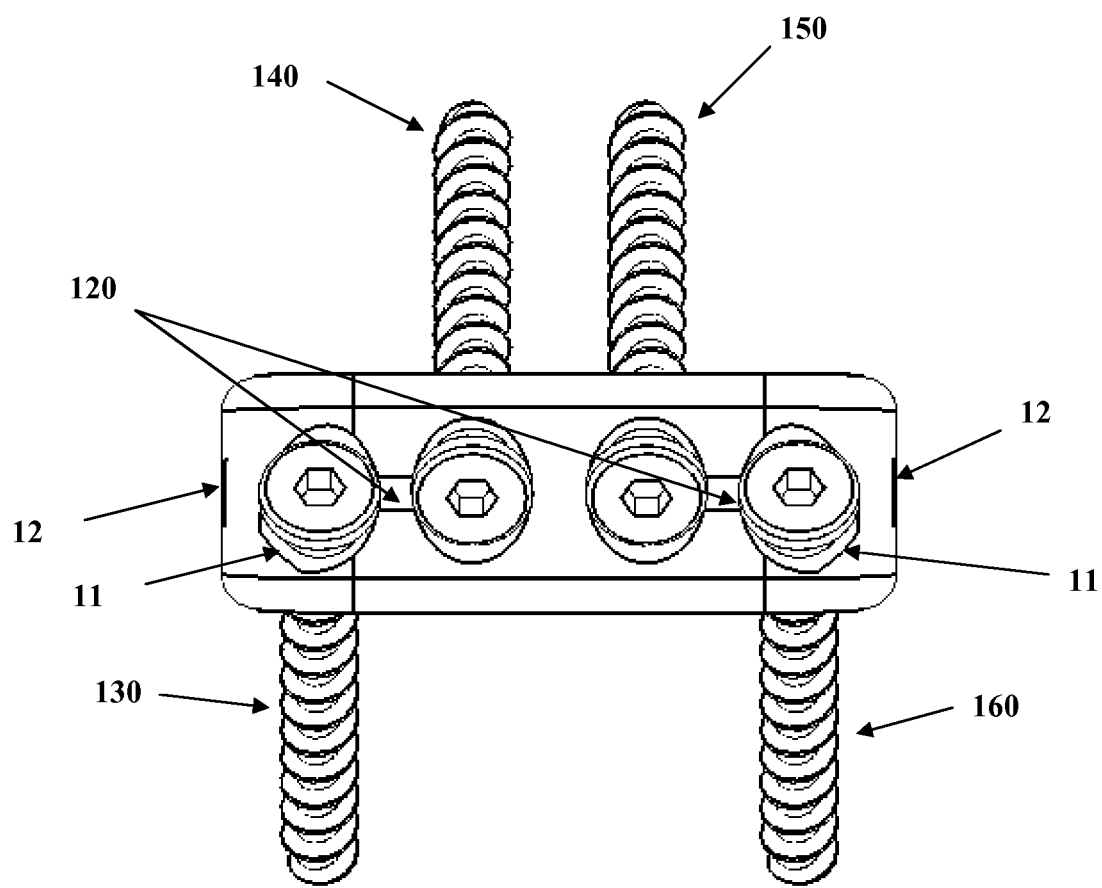
FIG. 4A illustrates a top view of an anterior lumbar intervertebral cage/BDFT screw construct according to an embodiment of the invention.
Figure 4B:
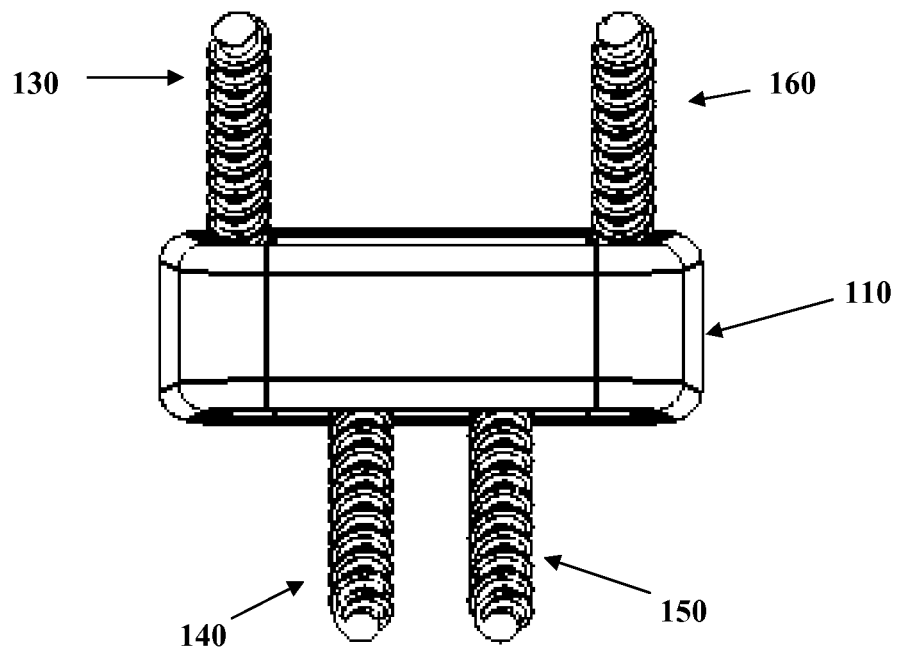
FIG. 4B illustrates a bottom view of an anterior lumbar intervertebral cage/BDFT screw construct according to an embodiment of the invention.
Figure 4C:
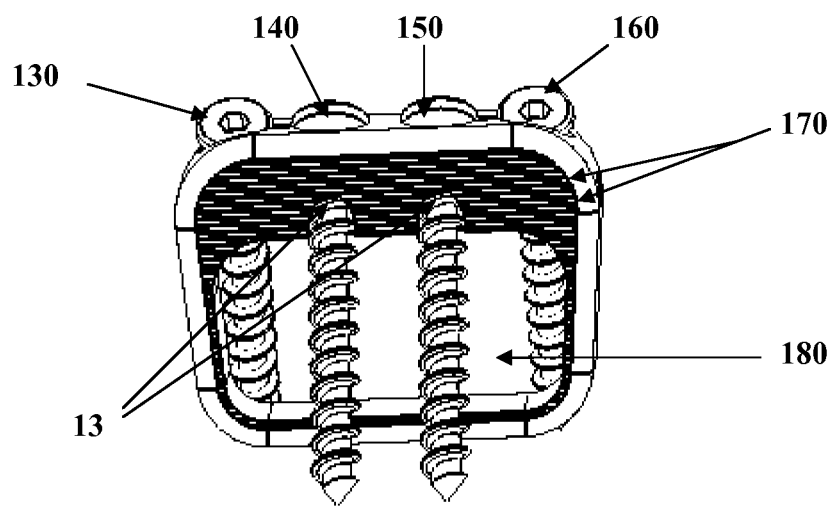
FIG. 4C illustrates a front view of an anterior lumbar intervertebral cage/BDFT screw construct according to an embodiment of the invention.
Figure 4D:
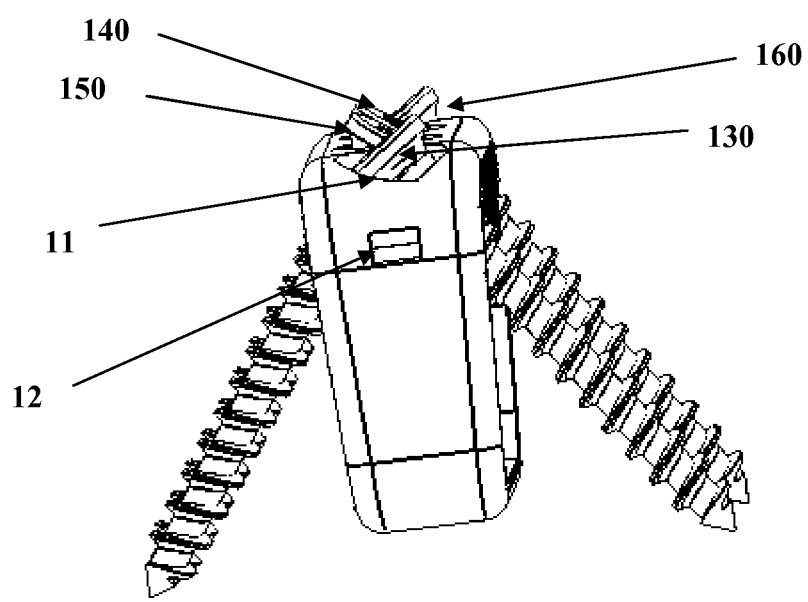
FIG. 4D illustrates a side, perspective view of an anterior lumbar intervertebral cage/BDFT screw construct according to an embodiment of the invention.
Figure 4E:
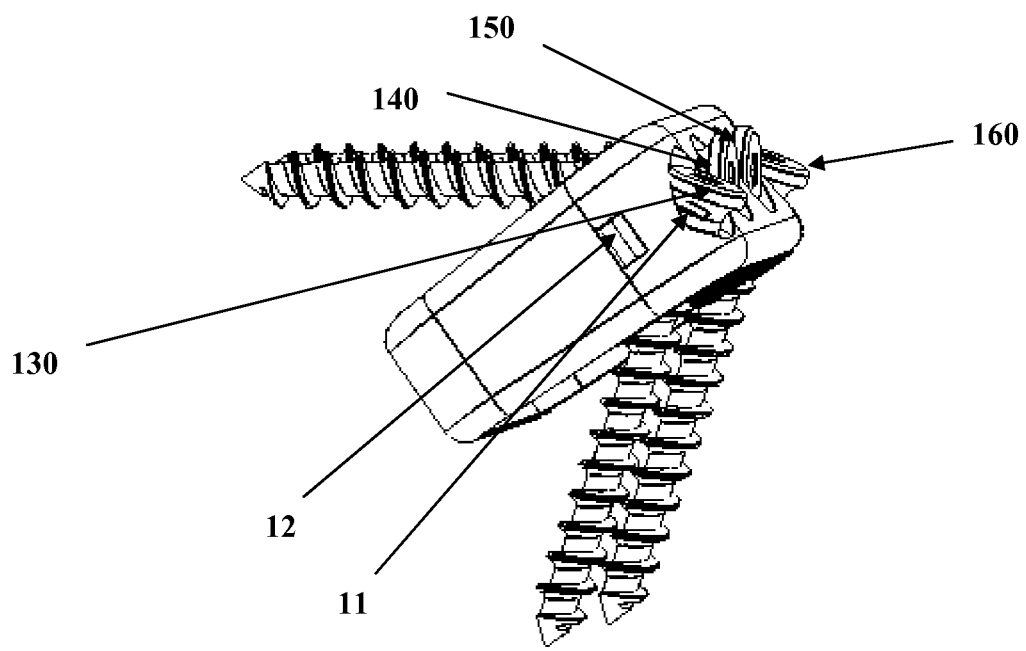
FIG. 4E illustrates a side perspective view of an anterior lumbar intervertebral cage/BDFT screw construct according to an embodiment of the invention.
Figure 4F:
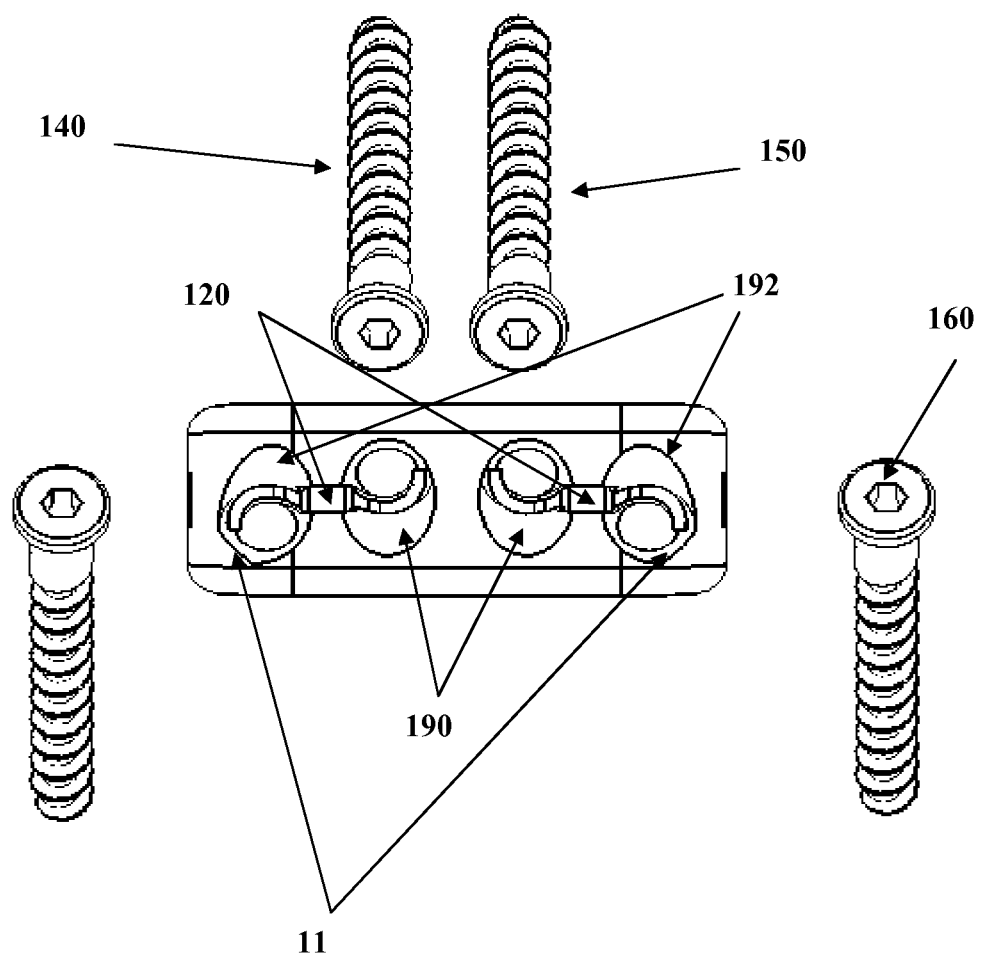
FIG. 4F illustrates a top, partially exploded view of an anterior lumbar intervertebral cage/BDFT screw construct according to an embodiment of the invention.
Figure 4G:
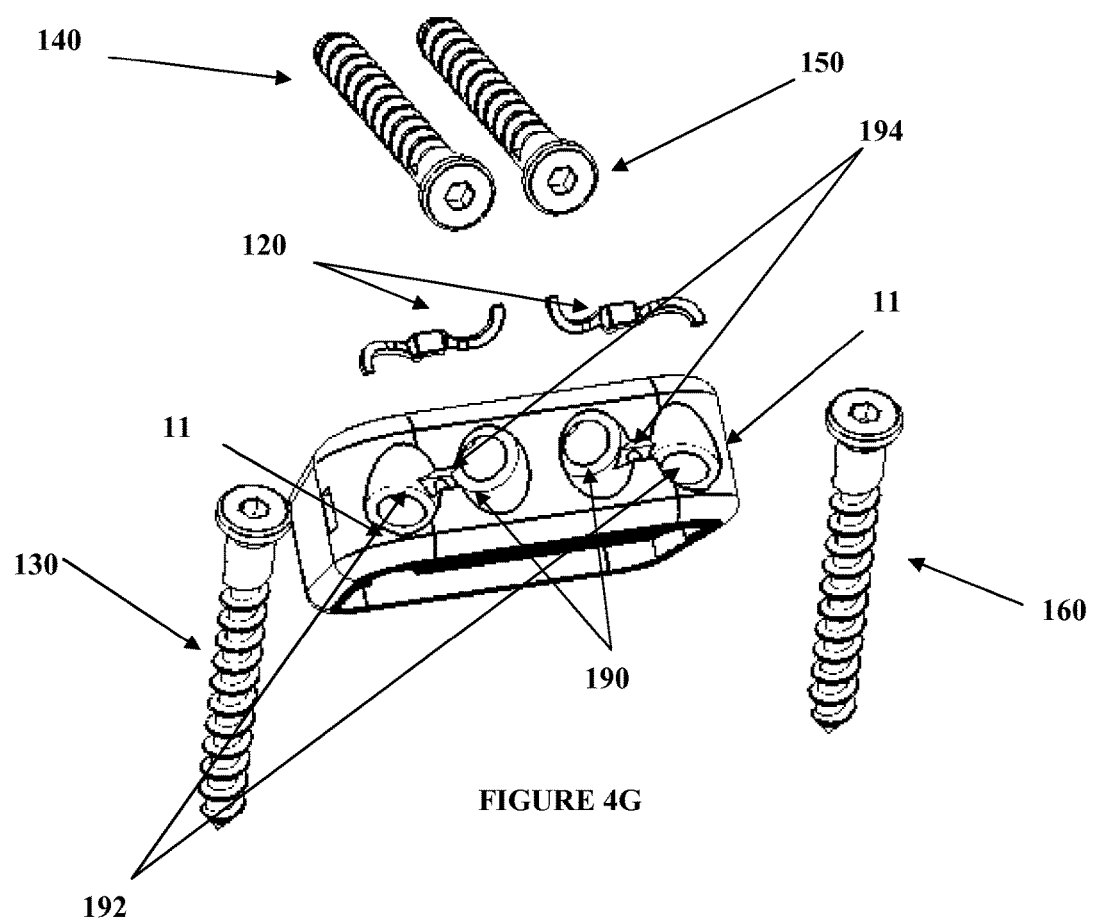
FIG. 4G illustrates a top, perspective, exploded view of an anterior lumbar intervertebral cage/BDFT screw construct according to an embodiment of the invention.

FIGS. 3A-3C and 4A-4G illustrate three-dimensional views of an exemplary embodiment of an anterior lumbar intervertebral cage/BDFT construct 110 having four internalized screw guides 190, 192. In this embodiment, the cage 110 can include indentations 11 on top of the cage 110 laterally adjacent to the first and fourth internalized screw guides 192 which function as independent or supplemental screw locking mechanisms. The cage 110 can include additional indentations or slots 12 on both side surfaces of the cage 110 for insertion of a prong of an implantation tool, and more particularly, that engage the distal medial oriented male protuberance of a lateral griper prong of an implantation tool. The cage 110 can be larger than the cervical cage 10 and also can be elliptically contoured when viewed from the side (e.g., along the side surfaces of the cage 110 in FIG. 4D) to fit into the bi-concave lumbar disc space. The cage 110 can include four (4) horizontally aligned internalized screw guides 190, 192 for four (4) screws 130, 140, 150, 160. The two lateral (left and right) screws 130, 160 can be oriented inferiorly, and the two middle screws 140, 150 can be oriented superiorly. The screw guide tunnel exits 13 are illustrated in FIGS. 3C and 4C. The screw guide tunnel exits 13 are in continuity (connected) with the enlarged bone cavity 180. In the embodiment, the orientations of the four screw guides 190, 192 (and screws 130, 140, 150, 160) are selected because of their symmetry and inherent stability.

The cage 110 can include a large cavity 180 for bone product placement. The cage 110 can include four built-in internalized screw/drill guides 190, 192 (e.g., having a preferred 25 degree angulation, or another angulation), one for each screw 130, 140, 150, 160. Other embodiments of the intervertebral cage 110 can be designed with internalized screw/drill guides 190, 192 with different angles and/or different positions within the cage 110. The angle and size of the screws make them amenable to single or multi-level placement. The superior and inferior surfaces or edges of the cage 110 can include ridges 170 to facilitate integration and fusion with superior and inferior vertebral bodies. In an embodiment, there are no compartmental divisions in the cavity 180 for bone product placement to maximize the quantity of bone for fusion.

The cage 110 includes two screw locking mechanisms 120 that can be, for example, press-fit to the top of the cage 110 (FIG. 4). In the embodiment, one locking mechanism 120 is provided per two screws. However, in other embodiments, one locking mechanism can be provided for each screw, or one locking mechanism can be provided for two or more screws. The top of the cage 110 can include a perforation 194 and/or an indentation 196 for each locking mechanism 120. Each locking mechanism 120 also can be designed to rest and be press-fit into the in-built self drilling screw guides 190, 192. The locking mechanism 120 can be manufactured from a variety of materials, such as titanium. In this embodiment, the cage 110 can include indentations 11 at the top of the cage adjacent to each lateral screw 130, 160, as illustrated for example in FIGS. 3A-4G, which indentations 11 function as independent or supplemental screw locking mechanisms. When the screws are turned into the screw locking mechanism 120, they lock by mechanically indenting the screw locking mechanism 120. The locking mechanism 120 can be reused for a limited number of cycles. In the absence of this locking mechanism, the screw can directly engage the cage indentations 11 adjacent to the screw guides 190, 192, which function as independent or supplemental screw locking mechanisms. This design is an evolutionary advance and improvement compared to the apparatus illustrated in the aforementioned related applications. It is quite unique and different from all other conventional locking mechanisms used for other types of anterior lumbar cages.

The exemplary embodiments of the present invention differ in many substantial ways from conventional devices that have been or are currently being developed.

For example, a possible conventional device conceivably may include anterior placed lumbar implants with perforating screws. Such a device may include, for example, a horseshoe implant having a plurality of cylindrical holes with smooth inner surfaces and comprise only one stop for the heads of the bone screws to be inserted into them. The placement of five cylindrical holes may be oriented within the cage in a non-symmetric manner.

In comparison, the exemplary embodiments of the present invention differ in many substantial ways from such devices. For example, the exemplary embodiments provide a symmetric orientation of the screw holes, as well as a screw locking mechanism. The exemplary embodiments also include an angulation/trajectory (e.g., a preferred angulation/trajectory) for preventing pull-out or back-out of the screws that would make placement of all screws in a manner which would lead to maximum stability of the construct within the vertebral space, and obviate the need for external drill guides, and surgeon trajectory angulation guess work.

In another conceivable conventional device, multiple embodiments of lumbar intervertebral implants may include internally threaded bore holes, without or with a front plate mounted at the front surface of the implant, and/or with a front plate displaceably configured to move vertically relative to the implant. Conventionally, the preferred borehole axes generally are 35-55 degrees. Conventional devices may have four screw perforations that are not aligned four in a row; e.g., two of the screw holes may be laterally placed on the left, one on top of each other, the top one with a superior trajectory, and the bottom with an inferior trajectory; and two perforations may be placed on the right, one on top of each other, the top one with a superior trajectory and the bottom one with an inferior trajectory. A possible screw locking mechanism may be a screw with an external thread matching the internal borehole thread, or spiral springs.

In comparison, the anterior lumbar construct of the exemplary embodiments differ in many substantial ways from these types of possible conventional devices. The exemplary embodiments can include a single cage construct with four (4) internalized drill guides arranged horizontally in a row. The middle two screws are oriented superiorly, and the lateral left and right screws are oriented inferiorly. This symmetric alignment of screws and orientations within the superior and inferior vertebral bodies (e.g., two middle superiorly projecting screws, and two laterally projecting inferior screws) make the fixation to the superior and inferior vertebral bodies much more symmetric and thus more stable. In an embodiment, the cage includes a screw guide having a predetermined trajectory (e.g., a preferred trajectory of 25 degrees) that makes placement of all screws equally facile, more amenable to multi-level placement, and diminishes the need for external drill guides. Furthermore, the exemplary screw locking mechanism, which is press-fit to the cage, is unique and differs substantially from the conventional approach of matching screw/cage threads or spiral springs. The exemplary cage further has novel indentations adjacent to the screw guides distributing the physical forces at the screw/cage interface stabilizing the construct and functioning as an independent or supplemental screw locking mechanism.

Figure 5A:
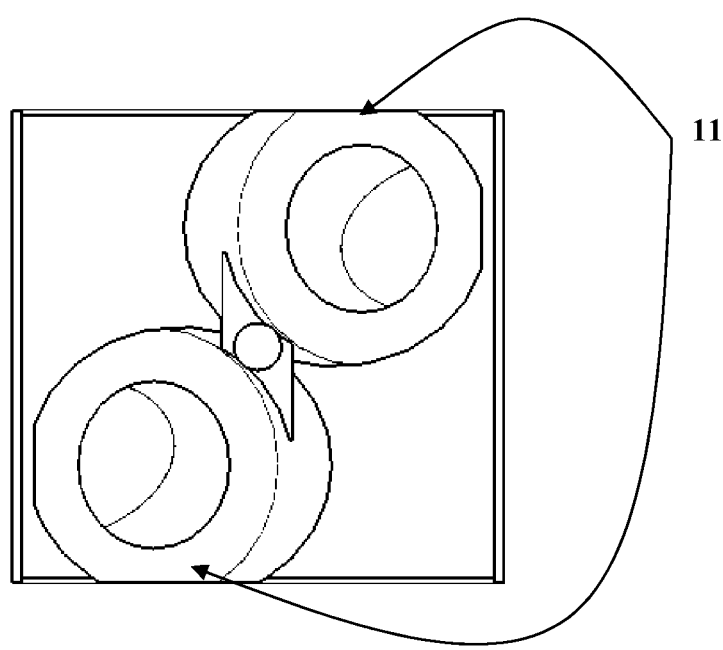
FIG. 5A illustrates a top view of a posterior Lumbar intervertebral cage with novel indentations according to an embodiment of the invention.
Figure 5B:
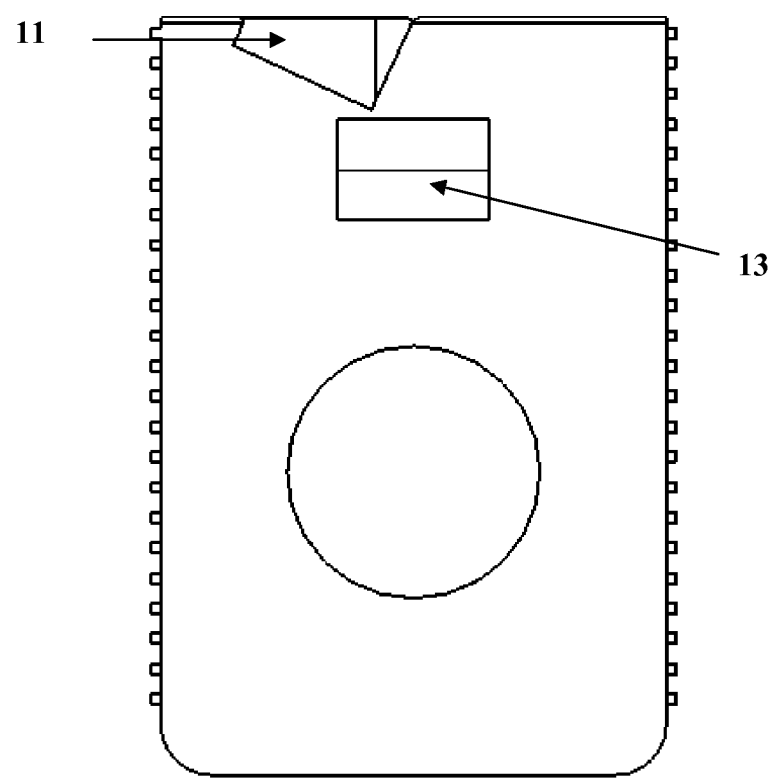
FIG. 5B illustrates a side (lateral) view of a posterior Lumbar intervertebral cage with novel indentations according to an embodiment of the invention.
Figure 5C:
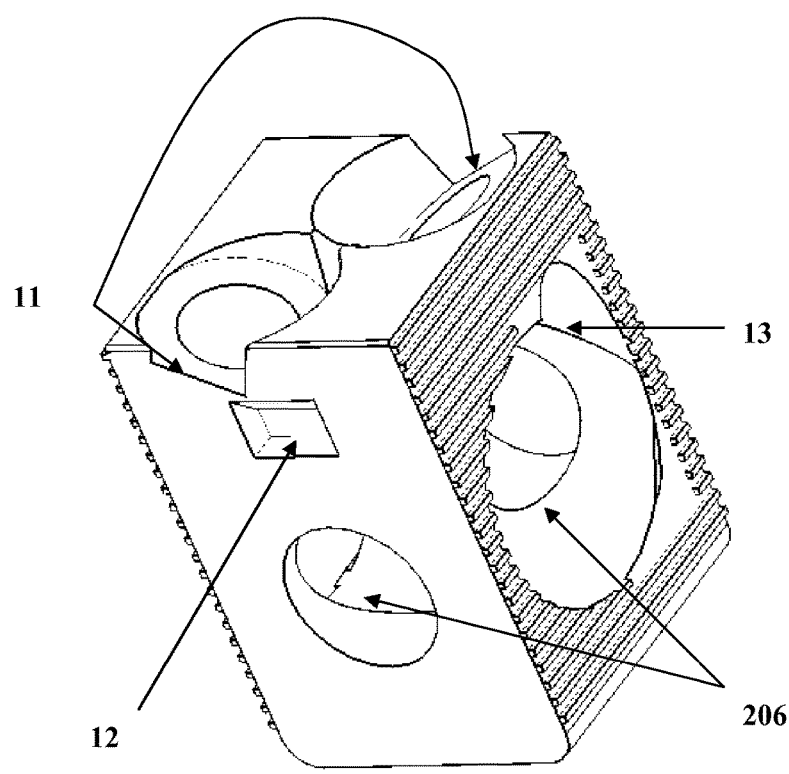
FIG. 5C illustrates a perspective (oblique) view of a posterior Lumbar intervertebral cage with novel indentations according to an embodiment of the invention.
Figure 6A:
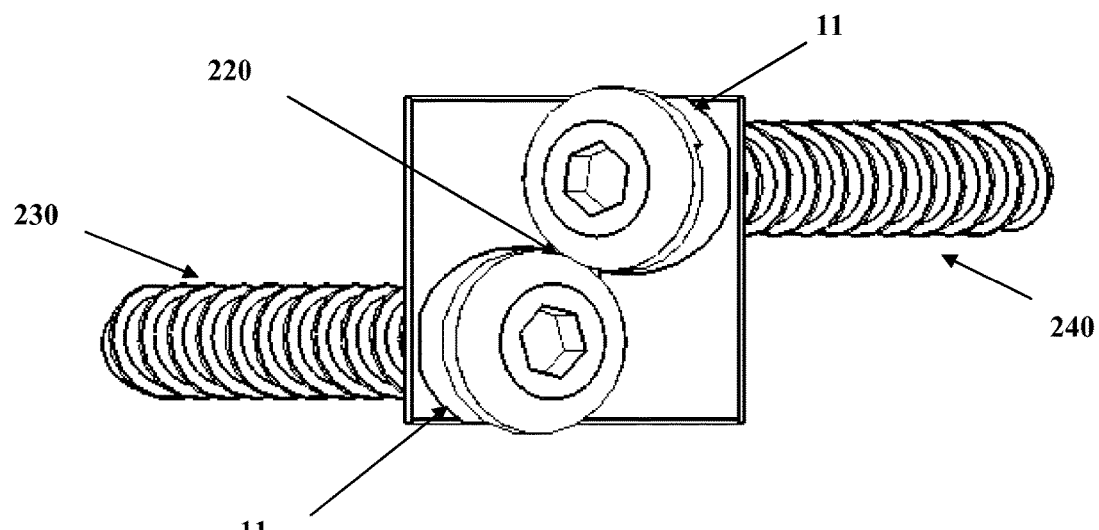
FIG. 6A illustrates top view of a posterior lumbar intervertebral cage/BDFT construct according to an embodiment of the invention.
Figure 6B:
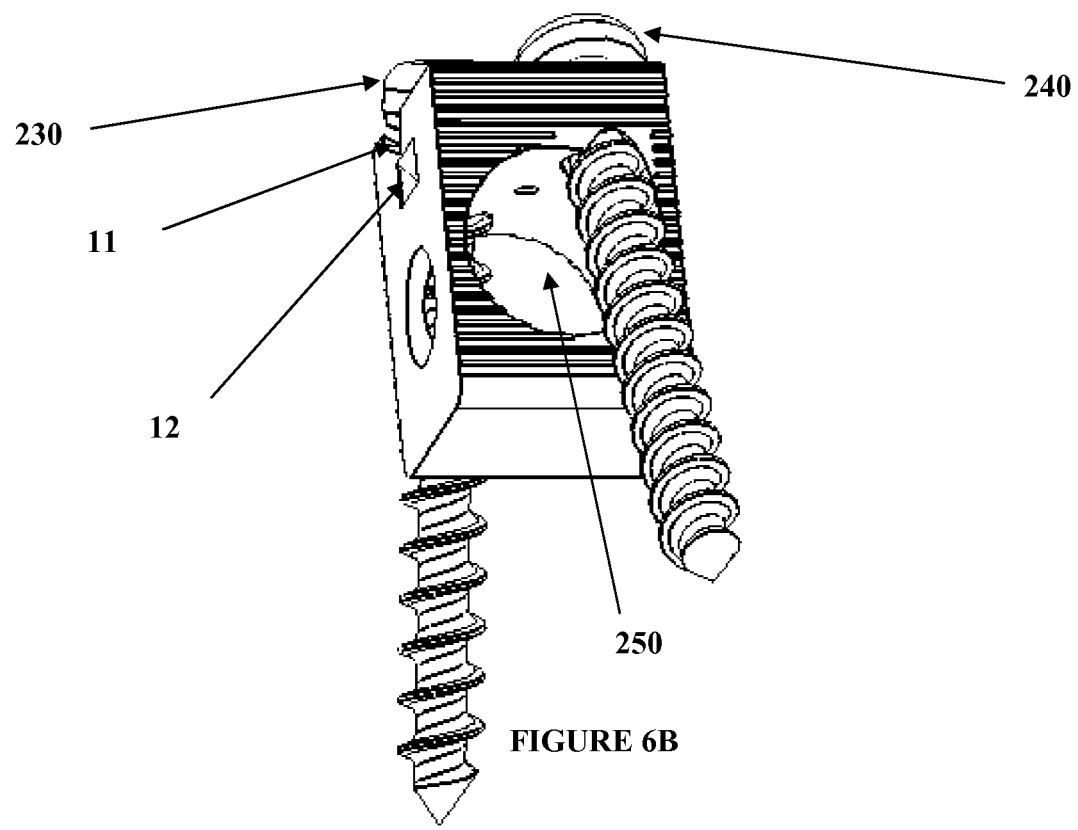
FIG. 6B illustrates bottom perspective view of a posterior lumbar intervertebral cage/BDFT construct according to an embodiment of the invention.
Figure 6C:
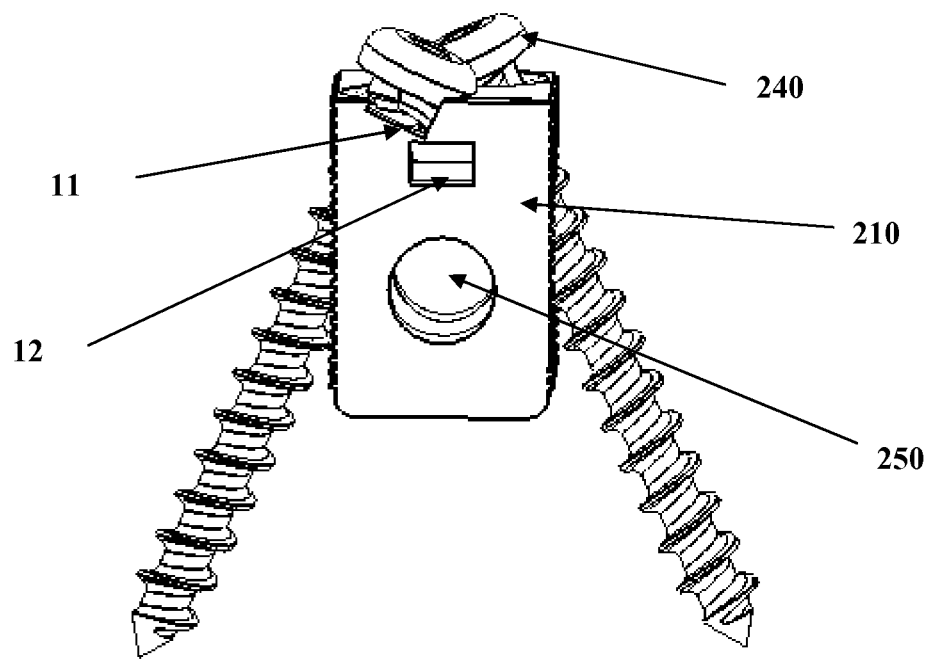
FIG. 6C illustrates side view of a posterior lumbar intervertebral cage/BDFT construct according to an embodiment of the invention.
Figure 6D:
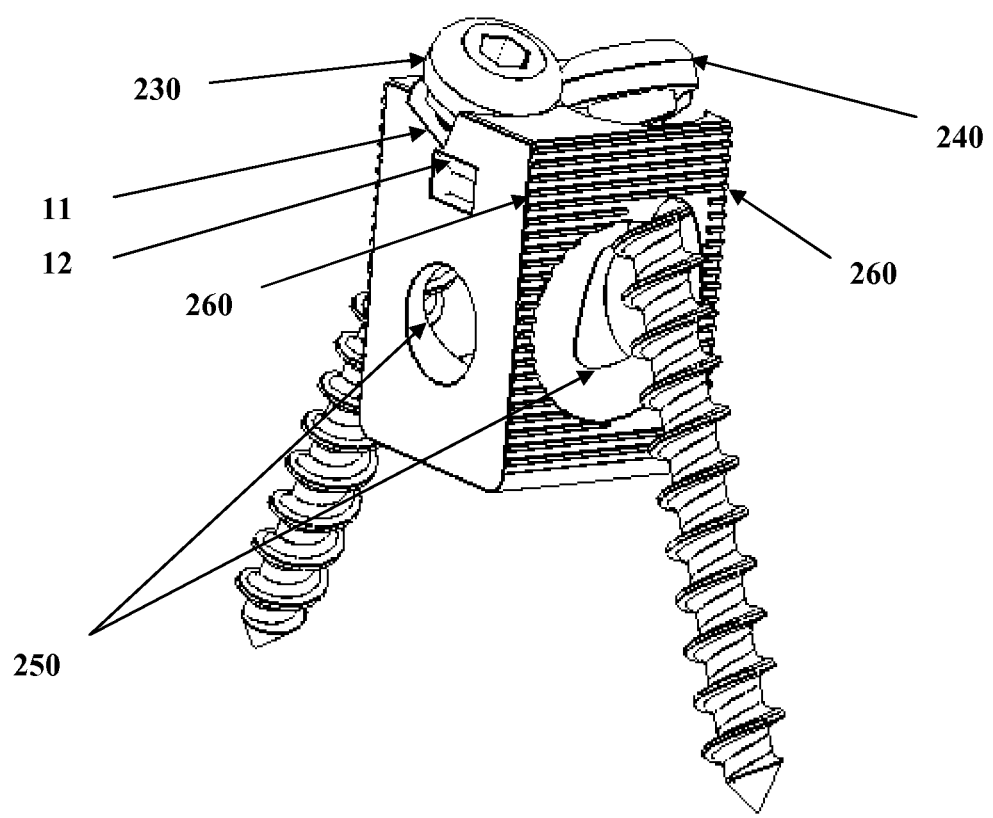
FIG. 6D illustrates perspective view of a posterior lumbar intervertebral cage/BDFT construct according to an embodiment of the invention.
Figure 6E:
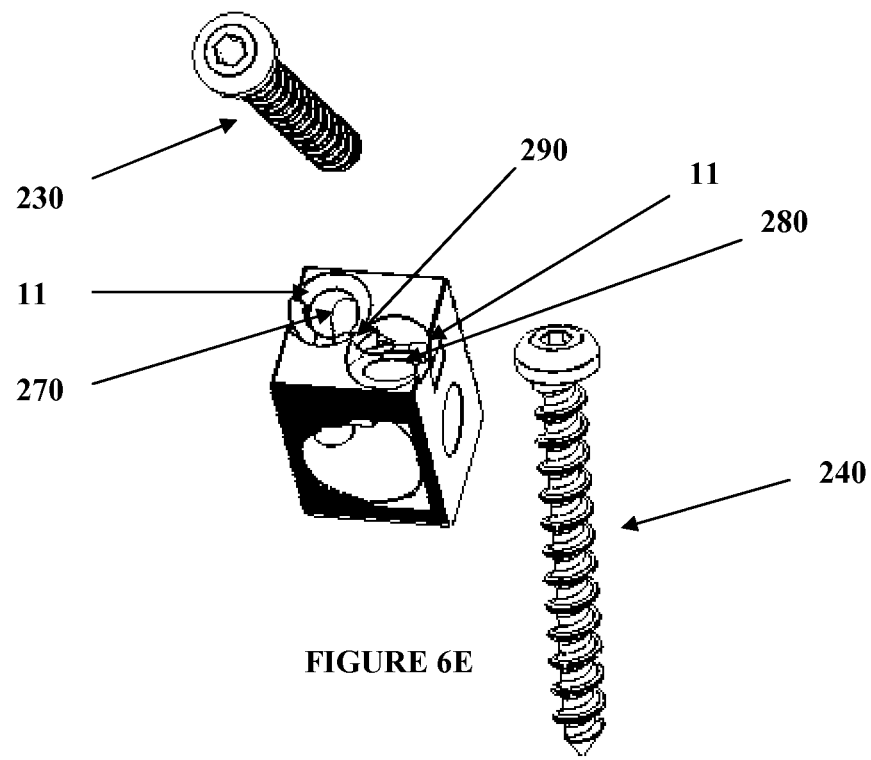
FIG. 6E illustrates top, perspective, partially exploded view of a posterior lumbar intervertebral cage/BDFT construct according to an embodiment of the invention.
Figure 6F:
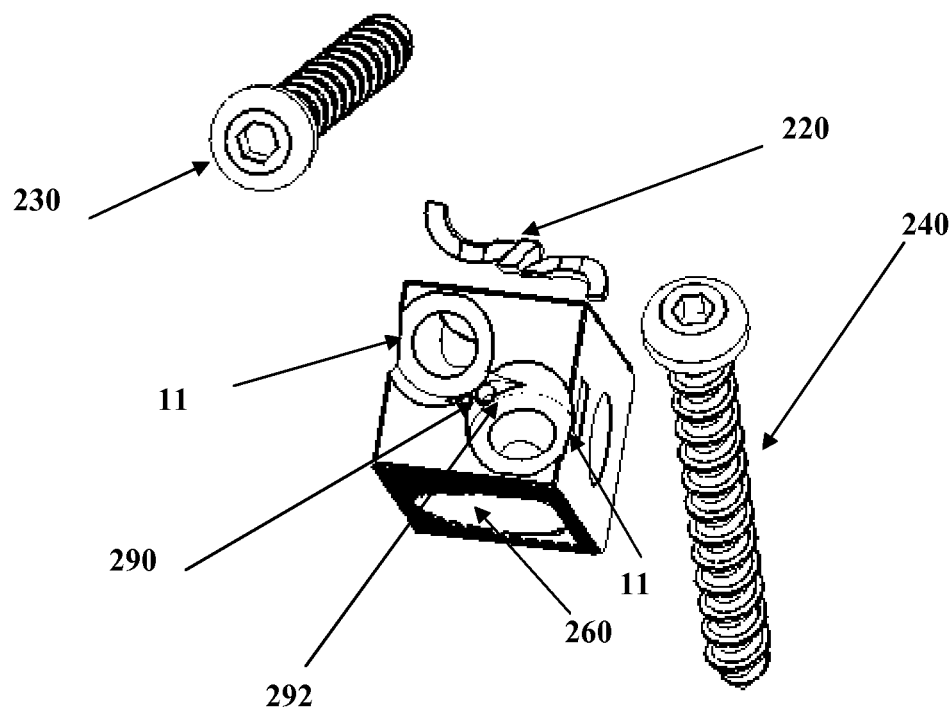
FIG. 6F illustrates top, perspective, exploded view of a posterior lumbar intervertebral cage/BDFT construct according to an embodiment of the invention.

FIGS. 5A-5C and FIGS. 6A-6F illustrate three-dimensional views of an embodiment of a posterior lumbar intervertebral cage/BDFT construct. In this embodiment, the cage 210 can include indentations 11 on top of the cage 210 that are adjacent to the internal screw guides 270, 280 (FIGS. 5A-5C). The indentations 11 can function as independent or supplemental screw locking mechanisms. The cage 210 also can include indentations 12 on both side surfaces of the cage 210 for placement of prongs of an implantation tool. The screws 230, 240 perforate and orient in opposing superior and inferior directions. The cage 210 can include a cavity 250 for bone product placement. The top and bottom portions of the cage 210 can be elliptically contoured to naturally fit into the bi-concave intervertebral disc space when viewed from the side as shown in FIG. 6C.

The cage 210 can include built-in internalized screw/drill guides 270, 280 having a predetermined angled trajectory (e.g., having a preferred 25 degree angulation). One of the guides is angled rostrally (superiorly) (e.g., guide 270) and the other caudally (inferiorly) (e.g., guide 280). The intervertebral cages 210 can be designed with internalized screw/drill guides 270, 280 with different angles and/or different positions within the cage 210. The angle and size of the screws 230, 240 make them amenable to single or multi-level placement. The screw guide tunnel exit 13 adjacent to the bone cavity 250 is exemplarily illustrated in FIG. 5C. The superior and inferior surfaces or edges of the cage 210 can include ridges 260 to facilitate integration and fusion with superior and inferior vertebral bodies. One of these constructs is placed posteriorly into the intervertebral space on the left side, and the other on the right side.

The cage 210 can include a screw locking mechanism 220 that can be, for example, press-fit to the top of the cage 210. The top of the cage 210 can have a perforation 290 and/or an indentation 292 to engage the locking mechanism 220.

The locking mechanism 220 also can be designed to rest and be press-fit into the in-built self drilling screw guides 270, 280. The locking mechanism 220 can be manufactured from a variety of materials, such as titanium. When the screws 230, 240 are turned into the screw locking mechanism 220, the screws 230, 240 lock by mechanically indenting the screw locking mechanism 220. The screw locking mechanism 220 can be reused for a limited number of cycles. In the absence of any locking mechanism, the screw head directly engages the cage's novel indentations 11 adjacent to the screw guides 270, 280, which indentations 11 can function as independent or supplemental screw locking mechanisms. The exemplary embodiment of this novel intervertebral cage 210 is an evolutionary advance and improvement compared to the apparatus illustrated in the aforementioned related applications. The novel cage 210 also is quite unique and different from other conventional locking mechanisms used for other known cervical and lumbar anterior or posterior plate screws. No other conventional posterior lumbar intervertebral cage BDFT/screw constructs are known.

2. Exemplary Surgical Method

Exemplary surgical steps for practicing one or more of the forgoing embodiments will now be described.

Anterior cervical spine placement of the intervertebral cage/BDFT screw construct (FIGS. 1A-2G) can be implanted via previously described techniques for anterior cervical discectomy and fusion. Some but not all of these techniques include, open, microscopic, closed endoscopic or tubular. Fluoroscopic or any other form of visualized guidance can be used for this procedure.

After the adequate induction of anesthesia the patient is placed in a supine position. An incision is made overlying the intended disc space or spaces, and the anterior spine is exposed. A discectomy is performed and the endplates exposed. The disc height is measured and an anterior cervical intervertebral cage of the appropriate disc height, width and depth is selected. The central cavity 60 of the cage 10 is packed with bone fusion material, autologous bone graft, allograft, alone or in combination with any commercially available bone fusion promoting product. The cage 10 is then inserted into the midline of the anterior disc space routinely until it is flush or countersunk relative to the vertebral body above and below. The BDFT screws 30, 40 are then inserted into the internalized rostrally (superiorly) and caudally (inferiorly) angled screw guides 80, 82. A drill with or without a drill guide can be used to prepare for screw placement. This is not absolutely necessary. Because the cage 10 has internalized screw guides 80, 82, self-drilling/self-tapping screws 30, 40 of the appropriately selected lengths can be directly screwed into the vertebral bodies once placed into the internalized drill-guided angled tunnels. The cage's screw guides 80, 82, which have internalized tunnels, direct the screws 30, 40 into the superior and inferior vertebral bodies in the predetermined angle of the internalized tunnels. There is no other angled trajectory other than that which is built into the internalized screw guide/tunnel 80, 82 of the cage 10 that the screw 30, 40 can be oriented in. Hence, there is no absolute need for fluoroscopic guidance.

Once the surgeon is satisfied with the position and placement of the cage 10, the BDFT screws 30, 40 can then be locked into their final positions by the last several turns which embed them into the novel surrounding cage indentations 11 as well as into the screw locking mechanism 20 thereby preventing screw blackout. If the surgeon changes his mind intra-operatively or if in a future date the construct needs to be removed, the screws 30, 40 can be backed out.

The locking mechanism 20 has several cycles of use, and thus screws 30, 40 once backed out, can be re-screwed and re-locked. Multiple level placements can be performed including two, three or more levels if necessary. With this modification it is not necessarily necessary to supplement with an additional screw locking mechanism. The novel indentations 11 themselves function as independent or supplemental screw locking mechanisms. Alternatively, one can choose to supplement the cage 10 with this or any other locking mechanism.

Anterior or anteriolateral placement of thoracic or lumbar spine intervertebral cage/BDFT screw constructs (FIGS. 3A-4E) can be implanted via previously described surgical techniques for anterior lumbar discectomy, and transthoracic, anterior-lateral thoracic discectomy. Some but not all of these techniques include, open, microscopic, closed endoscopic or tubular. Fluoroscopic or any other form of visualized guidance can be used for this procedure.

After the adequate induction of anesthesia and after the anterior spine is exposed a discectomy is performed and the endplates exposed. The disc height is measured and an anterior lumbar (or thoracic) intervertebral cage of the appropriate disc height, width and depth is selected. The central cavity 180 of the cage 110 is packed with bone fusion material, autologous bone graft, allograft, alone or in combination with any commercially available bone fusion promoting product. The cage 110 is then inserted into the midline of the anterior disc space routinely until it is flush or countersunk relative to the vertebral body above and below. The four BDFT screws 130, 140, 150, 160 are then inserted into the two middle internalized rostrally (superiorly) and two lateral, caudally (inferiorly) angled screw guides 190, 192. A drill with or without a drill guide can be used to prepare for screw placement. This is not absolutely necessary. Because the cage has internalized screw guides 190, 192, self-drilling/self-tapping screws 130, 140, 150, 160 of the appropriately selected lengths can be directly screwed into the vertebral bodies once placed into the internalized drill-guided angled tunnels 190, 192. The cage's internalized guides 190, 192, which have internalized tunnels, direct the screws 130, 140, 150, 160 into the superior and inferior vertebral bodies in the predetermined angle of the internalized tunnels. There is no other angled trajectory other than that which is built into the internalized screw guide/tunnel 190, 192 of the cage 110 that the screw 130, 140, 150, 160 can be oriented in. Hence there is no absolute need for fluoroscopic guidance.

Once the surgeon is satisfied with the position and placement of the cage 110, the BDFT screws 130, 140, 150, 160 can then be locked into their final positions by the last several turns which embed them into the novel surrounding cage indentations 11 and the screw locking mechanism 120, thereby preventing screw blackout. If the surgeon changes his mind intra-operatively or if in a future date the construct needs to be removed, the screws 130, 140, 150, 160 can be backed out. The locking mechanism 120 has several cycles of use, and thus screws 130, 140, 150, 160 once backed out, can be re-screwed and re-locked. Multiple level placements can be performed including two, three or more levels if necessary. Alternatively, in the absence of a screw locking mechanism 120, the heads of the screws 130, 140, 150, 160 can be embedded directly into the cage indentations 11 which function as independent or supplemental screw locking mechanisms, thereby preventing screw back out.

Implantation of the posterior lumbar intervertebral cage/BDFT screw constructs (FIGS. 5A-6F) can be performed via previously described posterior lumbar interbody fusion (PLIF) or posterior transforaminal lumbar interbody fusion (TLIF) procedures. The procedures can be performed open, microscopic, closed tubular or endoscopic techniques. Fluoroscopic guidance can be used with any of these procedures.

After the adequate induction of anesthesia, the patient is placed in the prone position. A midline incision is made for a PLIF procedure, and one or two parallel paramedian incisions or a midline incision is made for the TLIF procedure. For the PLIF procedure, a unilateral or bilateral facet sparing hemi-laminotomy is created to introduce the posterior lumbar construct into the disc space after a discectomy is performed and the space adequately prepared.

For the TLIF procedure, after unilateral or bilateral dissection and drilling of the inferior articulating surface and the medial superior articulating facet the far lateral disc space is entered and a circumferential discectomy is performed. The disc space is prepared and the endplates exposed.

The disc height is measured and a posterior lumbar intervertebral cage/BDFT screw construct (FIGS. 5A-6F) of the appropriate disc height, width and depth is selected. The central cavity 260 of the cage 210 is packed with bone fusion material, autologous bone graft, allograft, alone or in combination with any commercially available bone fusion promoting product. Then one construct/cage 210 is placed on either right or left sides, or one construct/cage 210 each is placed into left and right sides. The constructs/cages 210 are inserted such they are flush or countersunk relative to the superior and inferior vertebral bodies. In addition to the central cavities 260 that are packed with bone product, the intervertebral space in between the constructs/cages 210 can also be packed with bone product for fusion.

The BDFT screws 230, 240 are then inserted into internalized rostrally (superiorly) and caudally (inferiorly) angled screw guides 270, 280. A drill with or without a drill guide can be used to prepare for screw placement. This is not absolutely necessary. Because the cage 210 has internalized screw guides 270, 280, self-drilling/self-tapping screws 230, 240 of the appropriately selected lengths can be directly screwed into the vertebral bodies once placed into the internalized drill-guided angled tunnels. The cage's internalized guides 270, 280, which have internalized tunnels, direct the screws 230, 240 into the superior and inferior vertebral bodies in the predetermined angle of the internalized tunnels. There is no other angled trajectory other than that which is built into the internalized screw guide/tunnel 270, 280 of the cage 210 that the screw 230, 240 can be oriented in. Hence, unlike posterior placement of pedicle screws 230, 240 there is no absolute need for fluoroscopic or expensive and cumbersome, frameless stereotactic CT guidance.

Once the surgeon is satisfied with the position and placement of the cage(s) 210, the BDFT screws 230, 240 can then be locked into their final positions by the last several turns which embed them into the novel cage indentations 11 and the screw locking mechanism 220 thereby preventing screw back out. If the surgeon changes his mind intra-operatively or if in a future date the construct needs to be removed, the screws can be backed out. The locking mechanism has several cycles of use, and thus screws once backed out, can be re-screwed and re-locked. Alternatively in the absence of this screw locking mechanism 220, the screw heads can be directly embedded into the cage indentations 11 which can function as independent or supplemental screw locking mechanisms, thereby preventing screw back out. Multiple level placements can be performed including two, three or more levels.

The exemplary embodiments may provide effective and safe techniques that overcome the problems associated with current transpedicular based cervical, thoracic and lumbar fusion technology, as well as anterior cervical, thoracic and lumbar plating technology, and for many degenerative stable and unstable spinal diseases. These exemplary embodiments could replace many pedicle screw and anterior plating based instrumentation in many but not all degenerative spine conditions.

The speed and simplicity of placement of anterior and posterior lumbar intervertebral cage/BDFT screw constructs, and placement of anterior cervical cage/BDFT screw constructs according the exemplary embodiments, far exceeds that of current pedicle screw and anterior spinal plating technology. Furthermore, these exemplary devices have markedly significantly decreased risk of misguided screw placement and hence decreased risk of neurovascular injury, and blood loss. The lumbar and cervical intervertebral cage/BDFT screw constructs according to the exemplary embodiments all would have decreased recovery time, and more rapid return to work time compared to pedicle screw, and plating technology. These exemplary devices with great probability lead to similar if not equal fusion rates, with substantially less morbidity, and hence, overall, make them a major advance in the evolution of spinal instrumented technology leading to advances in the compassionate care of the spinal patient.

Figure 7A:
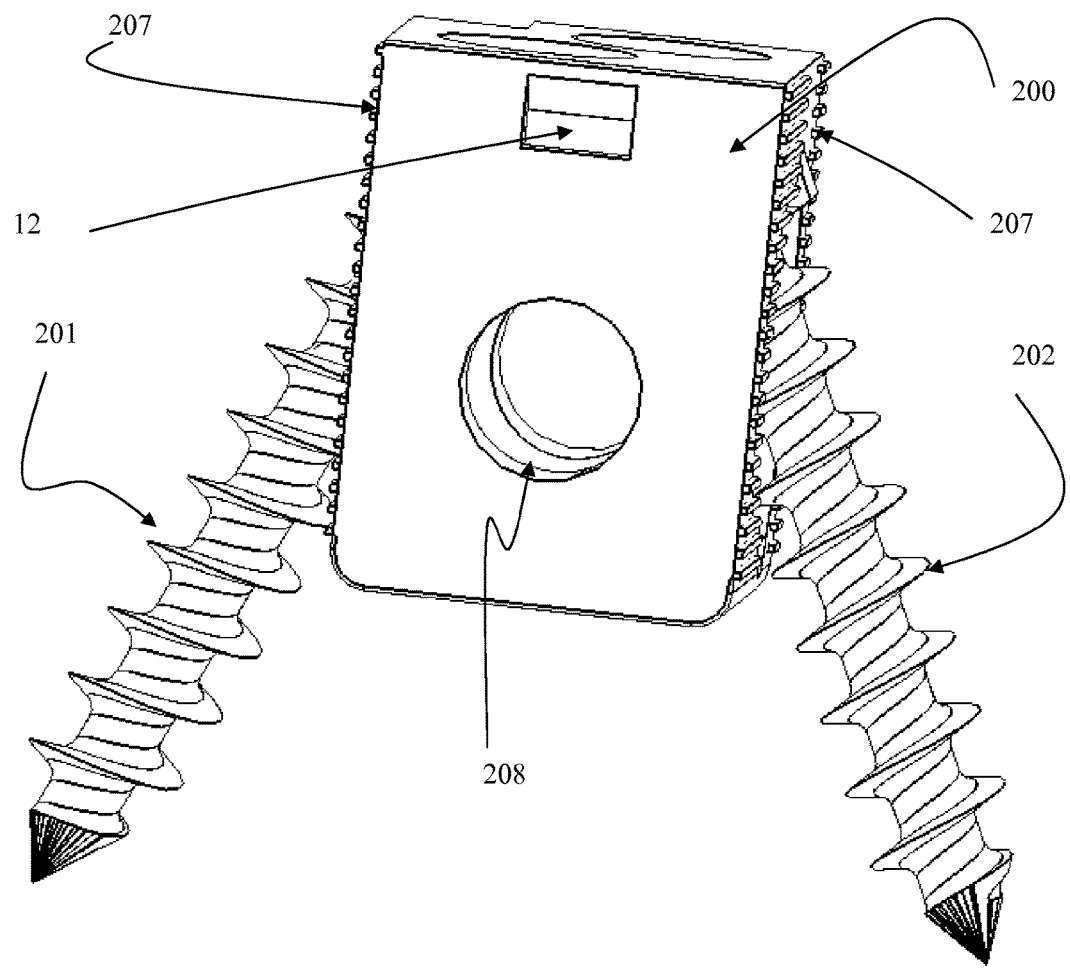
FIG. 7A illustrates a perspective view of an intervertebral cage construct according to an embodiment of the invention.
Figure 7B:
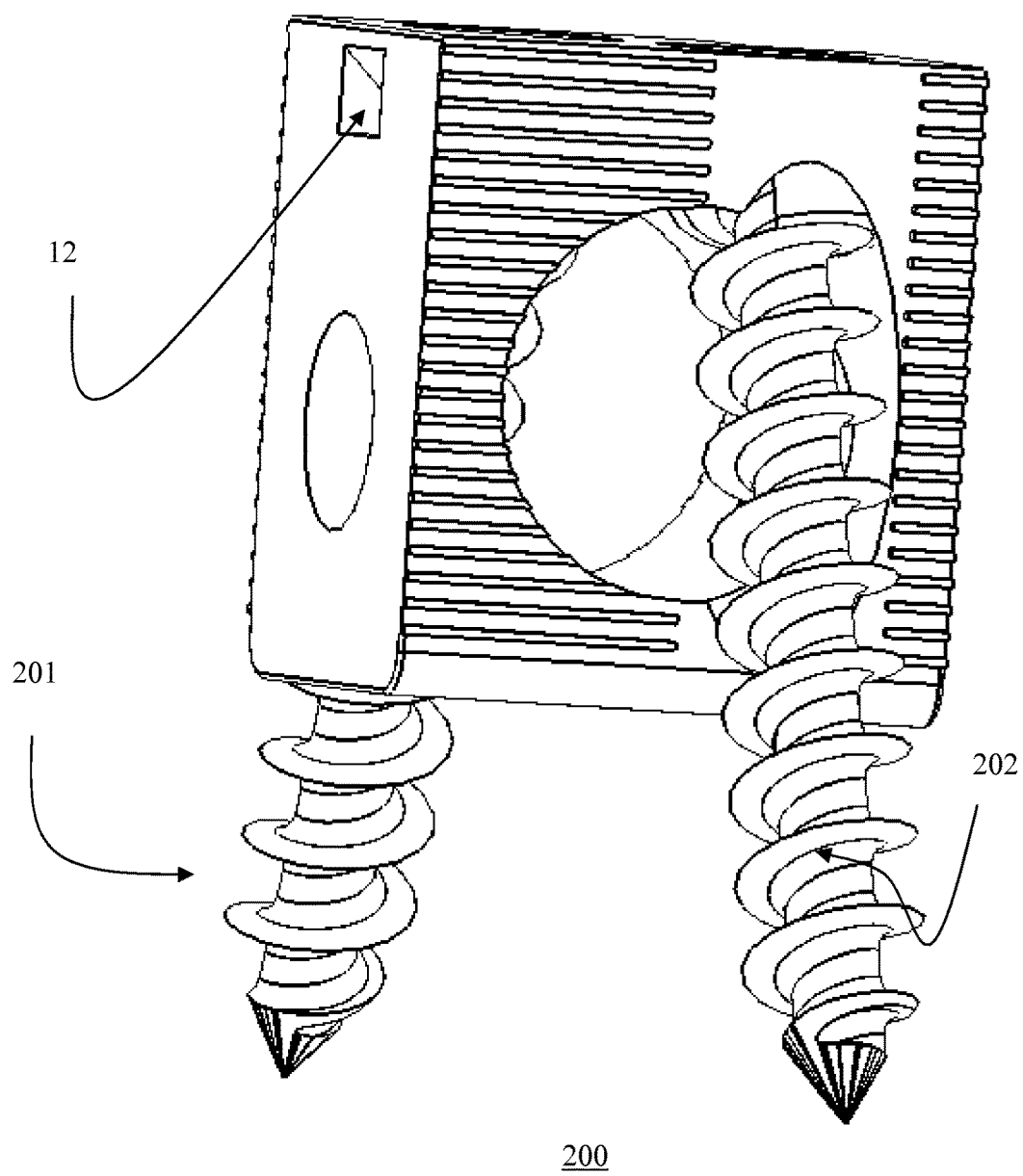
FIG. 7B illustrates another perspective view of an intervertebral cage construct according to an embodiment of the invention.
Figure 7C:
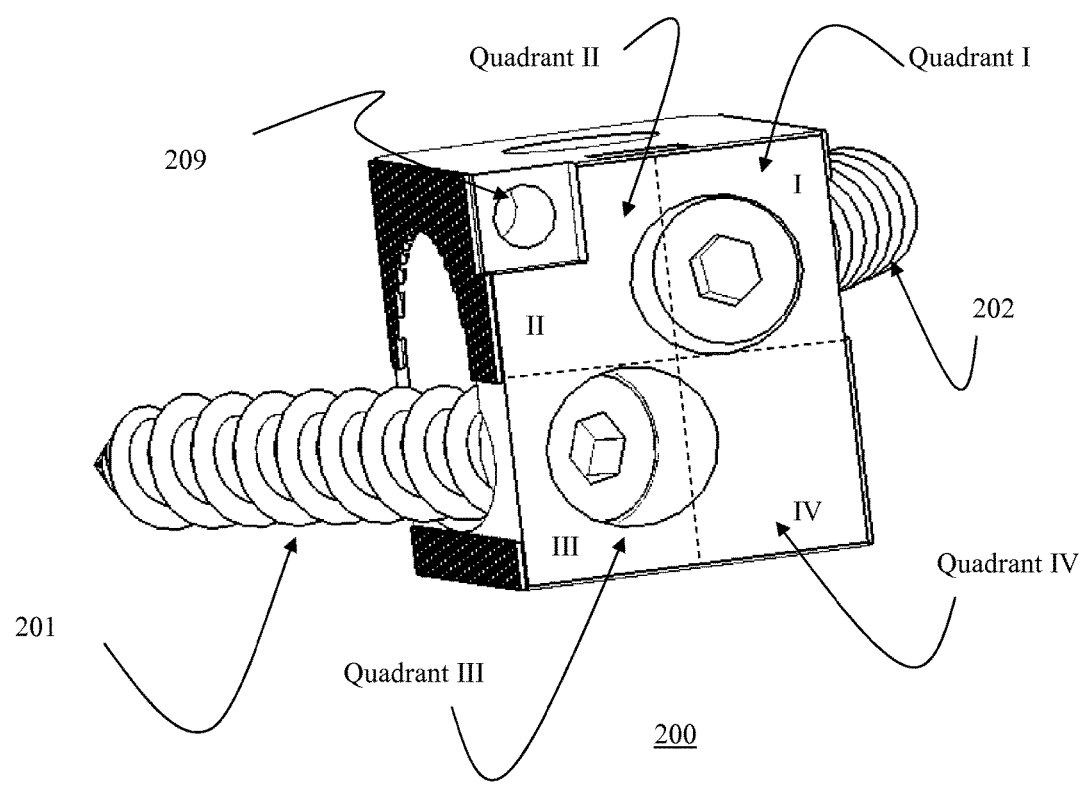
FIGS. 7C(i) and 7C(ii) illustrate top, perspective view of an intervertebral cage construct according to an embodiment of the invention.

FIGS. 7A, 7B, 7C(i), and 7C(ii) illustrate an exemplary embodiment of exemplary cage 200. These features are not limited to the cage 200, and can be incorporated into any cage according to any of the embodiments described herein. As shown in FIGS. 7C(i) and 7C(ii), the screw guides can be positioned within four (4) quadrants I, II, III, IV.

For example, the intervertebral cage can include a wall having an entry opening of the first integral screw guide and an entry opening of the second integral screw guide, wherein the wall of the cage can include four quadrants delineated by a first axis and a second axis each lying in a plane of the wall, and the first axis is at a right angle with respect to the second axis, wherein the four quadrants include a first quadrant, a second quadrant, a third quadrant, and a fourth quadrant, wherein the first quadrant and the fourth quadrant are opposed to the second quadrant and the third quadrant with respect to the first axis, and the first quadrant and the second quadrant are opposed to the third quadrant and the fourth quadrant with respect to the second axis, wherein the first quadrant is diagonally opposed to the third quadrant, and the second quadrant is diagonally opposed to the fourth quadrant, and wherein one of a majority of an area of the entry opening of the first integral screw guide is in the first quadrant and a majority of an area of the entry opening of the second integral screw guide is in the third quadrant; and the majority of the area of the entry opening of the first integral screw guide is in the second quadrant and the majority of the area of the entry opening of the second integral screw guide is in the fourth quadrant.

In an embodiment, the intervertebral cage can include a wall having an entry opening of the first integral screw guide and an entry opening of the second integral screw guide, wherein the wall has four quadrants delineated by a first axis and a second axis each lying in a plane of the wall, and the first axis is at a right angle with respect to the second axis, wherein the four quadrants include a first quadrant, a second quadrant, a third quadrant, and a fourth quadrant, wherein the first quadrant and the fourth quadrant are opposed to the second quadrant and the third quadrant with respect to the first axis, and the first quadrant and the second quadrant are opposed to the third quadrant and the fourth quadrant with respect to the second axis, wherein the first quadrant is diagonally opposed to the third quadrant, and the second quadrant is diagonally opposed to the fourth quadrant, and wherein one of a center of the entry opening of the first integral screw guide is in the first quadrant and a center of the entry opening of the second integral screw guide is in the third quadrant; and the center of the entry opening of the first integral screw guide is in the second quadrant and the center of the entry opening of the second integral screw guide is in the fourth quadrant.

Figure 7D:
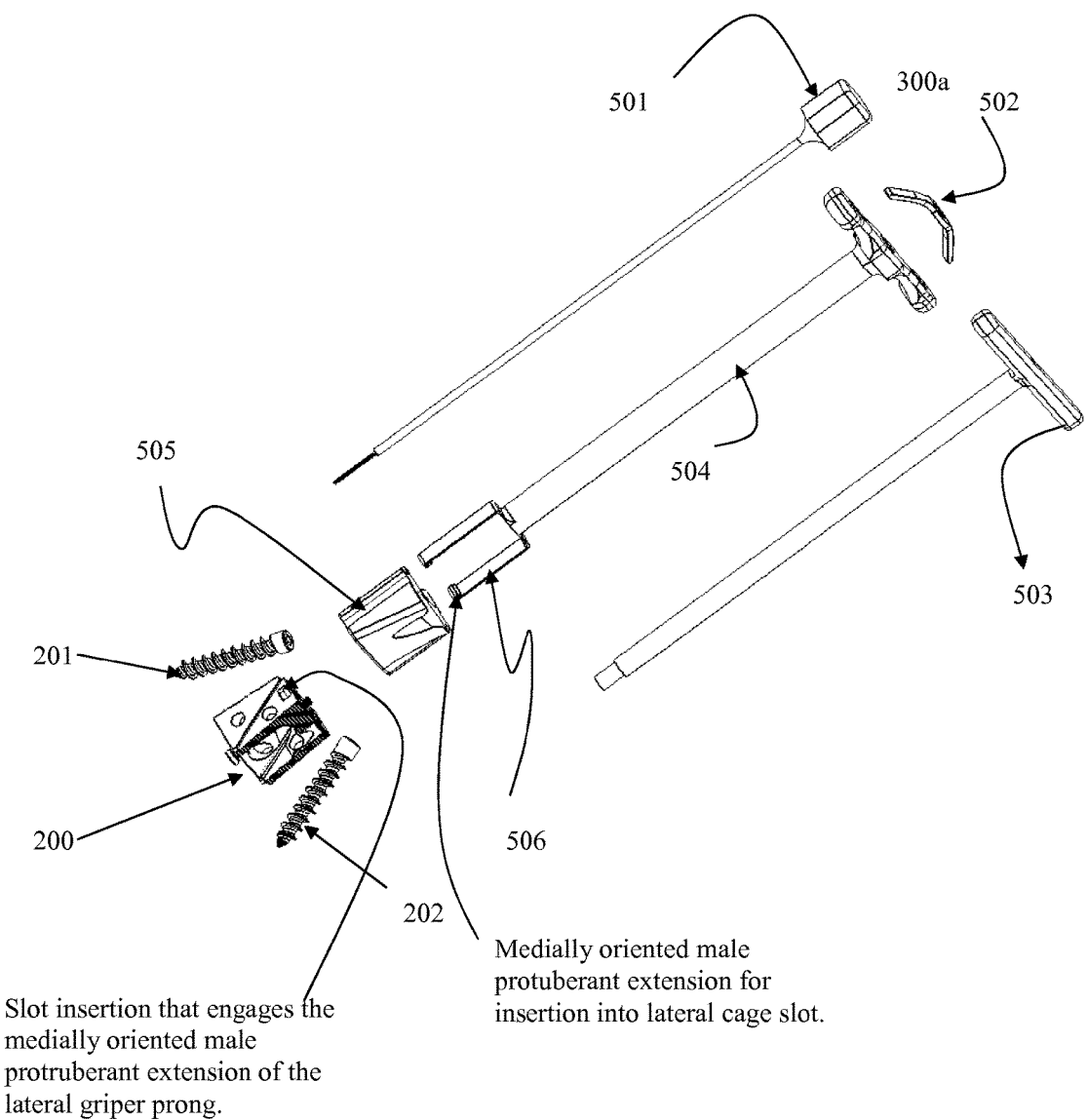
FIG. 7D illustrates a top, perspective, exploded view of a positioning tool/screw guide/box expander.

FIG. 7D illustrates an embodiment of an external drill/screw guide-box expander which assists in screw trajectory of the exemplary cage 200. The cage 200 can be a cage according to any of the embodiments described herein, or an expanding cage, in which case an expanding Allen key component can be used. The device can include, for example, an Allen key 501 (e.g., for an expandable cage), a spring 502, a handle 503, a griper 504, and a screw guide 505.

Figure 7E:
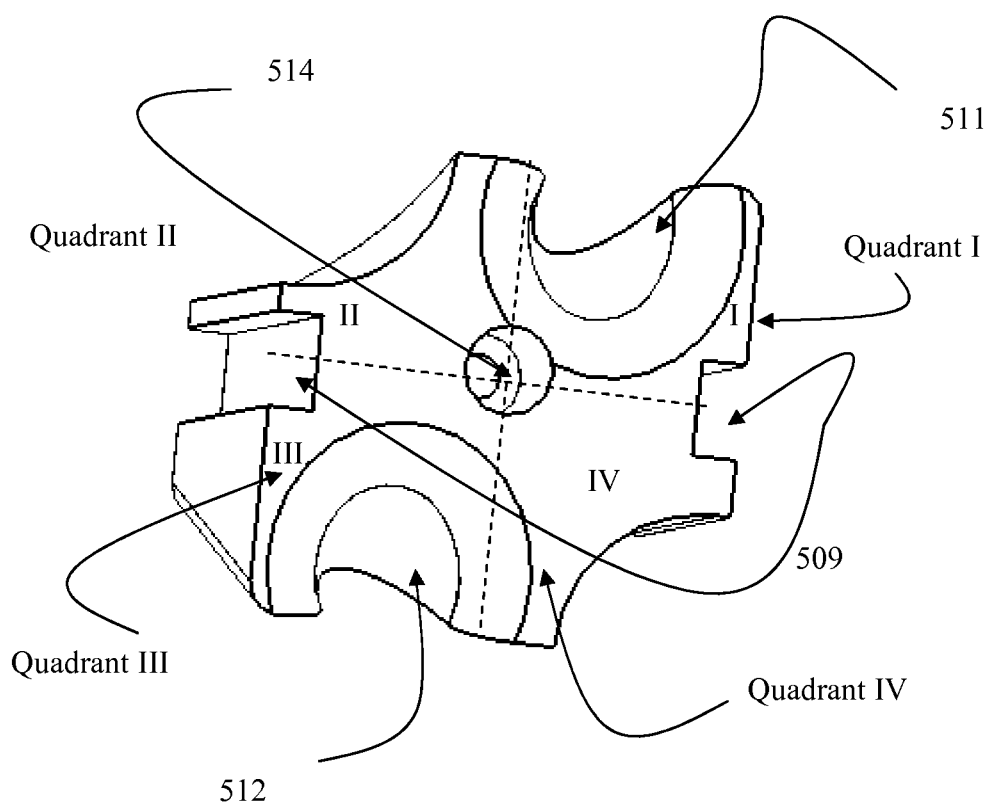
FIG. 7E illustrates a superior oblique perspective view of the positioning tool/drill guide/box expander component.

FIG. 7E illustrates a superior oblique view of the screw guide demonstrating insertions or grooves 509 for griper prong 506 of the griper 504 in FIG. 7D, built-in trajectory guides 511, 512 for insertions of screws, and an opening 514 for an Allen key.

The griper 504 has griper prongs (e.g., medially oriented male protuberant extensions) 506 which insert into grooves 509 of the screw guide 505 and lateral slots (e.g., 12) of the cage, thereby perfectly aligning them.

Hence, according to the exemplary embodiments, a cage can be provided that has internal screw guides which have no gaps, and furthermore an insertion tool can be provided that has an external screw guide that further precisely guides the screws through the external tool screw guide, then into the internal implant screw guide guaranteeing the precise predetermined angulation of the screws. The combination the internal and external screw guides can create a long tunnel for a screw to enable a predetermined trajectory.

It is noted that the same trajectory can be provided by only with the internal box screw guides; however, one of ordinary skill will recognize that having the external screw guides as part of the tool further maintains the precise angle trajectory. The screw guide positions within the four (4) quadrants I, II, III, IV conform to the screw guide positions within the four (4) quadrants I, II, III, IV of the screw box.

With reference to the drawings, it will be understood that an embodiment of the indentations or recesses for the screw holes in any of the exemplary cages can be configured such that the screw heads will rest entirely within a peripheral side of a surface of the top portion of the cage (i.e., top surface). In this embodiment, the direction of the screw tunnel is from an anterior surface to a posterior of the top surface of the cage (i.e., the non-adjacent side).

In another embodiment, the indentations or recesses for the screw holes can be configured such that the screw heads will rest entirely within the peripheral side of the top surface of the cage. In this embodiment, the screw hole guide passes through the anterior-posterior axis of the top surface. The guides core circumference for the screw thread is surrounded by the lateral wall masses, and surrounded by mass from the front and rear surfaces (i.e., walls) of the cage.

In yet another embodiment, the indentations or recesses for the screw holes can be configured such that a recess for the screw holes are entirely within the peripheral side of the top surface of the box. In this embodiment, there is a through-hole for a screw which is counter-bored to keep the screw head within an outer surface boundary of the cage and in a direction to prevent the screw from avoiding the front or rear surfaces of the cage.

In yet another embodiment, the indentations or recesses for the screw holes can be configured such that a recess for the screw holes is entirely within the peripheral side of the front wall of the cage In this embodiment, the tunnel for the screws is such that when the screw first enters, the screw will be surrounded by mass from the lateral sides and mass from the upper and lower sides of the wall. The screw will exit at the posterior end of the peripheral wall.

With reference to the drawings, it will be understood that an embodiment of the indentations or recesses for the screw holes can be configured such that a position of the screws is suitable for posterior lumbar screw holes.

For example, in an embodiment, the screw holes can be diagonal to each other along a transversal line. The transversal line can be defined as the line that would diagonally intersect and bypass the space between the recess for the screw holes.

In another embodiment, the screw holes can be diagonally opposed and lie on a congruent angle to each other from the intersecting transversal line.

In another embodiment, the recess for the screw holes can be diagonal and perpendicular to each other within the outer plane.

In another embodiment, the recess for the screw holes can be diagonal and symmetrically constrained within the outer wall of the cage.

While the foregoing disclosure shows illustrative embodiments of the invention, it should be noted that various changes and modifications could be made herein without departing from the scope of the invention as defined by the appended claims. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated.

What is claimed is:

1. An intervertebral combination internal screw guide and fixation apparatus configured to be inserted into a disc space between a first vertebral body and a second vertebral body and to provide fusion of the first vertebral body to the second vertebral body via biological bone fusion and screw fusion, the apparatus comprising:
   an intervertebral spacer including a top wall, a bottom wall, and first and second sidewalls, wherein the intervertebral spacer defines:
      an open space between the top, bottom, first, and second sidewalls capable of receiving bone filling for biological bone fusion,
      a first slot on a first outer side of the first sidewall,
      a second slot on a second outer side of the second sidewall of the two sidewalls, wherein the second slot is positioned opposite of the first slot, wherein the first slot is positioned along a first centerline axis that bisects the first side wall and wherein the second slot is positioned along a second centerline axis that bisects the second side wall,
      a first internal screw guide having a first entry opening and a first exit opening, the first entry opening of the first internal screw guide formed at least partially in a top surface of the top wall and the first exit opening formed at least partially in a bottom surface of the top wall and at least partially in a first side surface of the top wall,
      a second internal screw guide having a second entry opening and a second exit opening, the second entry opening of the second internal screw guide formed at least partially in the top surface of the top wall and the second exit opening formed at least partially in the bottom surface of the top wall and at least partially in a second side surface of the top wall so as to extend in a direction different than that of the first internal screw guide,
      an indentation in the top surface of the top wall extending between at least a portion of the first internal screw guide and the second internal screw guide, and
      a hole extending into the top wall at an angle that is perpendicular to the top surface of the top wall and at a position that is located in the indentation between the first internal screw guide and the second internal screw guide,
   a first screw having a first screw head and a first threaded body that is sized and configured to be inserted through the first internal screw guide;
   a second screw having a second screw head and a second threaded body that is sized and configured to be inserted through the second internal screw guide; and
   a screw locking mechanism positioned in the indentation of the intervertebral spacer and extending at least partially into the hole.

2. The apparatus of claim 1, wherein the screw locking mechanism comprises means for preventing the first and second screw from pulling out of the first and second internal screw guides.

3. The apparatus of claim 1, wherein the intervertebral spacer further defines:
   a third internal screw guide having a third entry opening and a third exit opening, the third entry opening of the third internal screw guide formed in the top surface of the top wall and the third exit opening formed at least partially in the bottom surface of the top wall and at least partially in the first side surface of the top wall, and
   a fourth internal screw guide having a fourth entry opening and a fourth exit opening, the fourth entry opening of the fourth internal screw guide formed in the top surface of the top wall and the fourth exit opening formed at least partially in the bottom surface of the top wall and at least partially in the second side surface of the top wall.

4. The apparatus of claim 1, wherein the screw locking mechanism comprises a narrow portion that is positioned in the hole and a wider portion that is positioned in the indentation, wherein the narrow portion extends from the wider portion into the hole.

5. The apparatus of claim 1, wherein the hole is a circular hole.

6. The apparatus of claim 1, wherein the intervertebral spacer further defines:
   a first circular side hole extending into the first outer surface of the first sidewall; and
   a second circular side hole extending into the second outer surface of the second sidewall, wherein the second circular side hole is positioned opposite of the first circular side hole, wherein the first slot and the first circular side hole are both positioned along the first centerline axis that bisects the first side wall and wherein the second slot and the second circular side hole are both positioned along the second centerline axis that bisects the second side wall.

7. The apparatus of claim 1, wherein the top wall is continuous with the first and second sidewalls.

8. The apparatus of claim 1, wherein the open space extends from an inner surface of the first sidewall to an inner surface of the second sidewall and extends from an inner surface of the top wall to an inner surface of the bottom wall.

9. The apparatus of claim 1, and further comprising means for facilitating integration and fusion with superior and inferior vertebral bodies.

10. The apparatus of claim 9, wherein the means is positioned at least partially on the first side surface of the top wall between the top surface of the top wall than the first exit opening.

11. The apparatus of claim 1, wherein the first side surface of the top wall is patterned with a plurality of surface features to create a first rough side surface, wherein at least some of the plurality of surface features are positioned on the first side surface between the top surface of the top wall and the first exit opening.

12. The apparatus of claim 11, wherein the plurality of surface features are patterned all the way to the top surface of the top wall such that at least one or more of the surface features are positioned on the side surface of the top wall adjacent to the top surface of the top wall.

13. The apparatus of claim 3, wherein the first side surface of the top wall is patterned with a plurality of surface features to create a first rough side surface, wherein at least some of the plurality of surface features are positioned on the first side surface between the top surface of the top wall and each of the first and third exit openings, wherein the second side surface of the top wall is patterned with the plurality of surface features to create a second rough side surface, wherein at least some of the plurality of surface features are positioned on the second side surface between the top surface of the top wall and each of the second and fourth exit openings.

14. The apparatus of claim 1, wherein a diameter of the hole is smaller than a diameter of the first and second internal screw guides.

15. The apparatus of claim 1, wherein the open space extends continuously from the first sidewall to the second sidewall.

16. A system comprising:
The apparatus of claim 1; and
a tool for manipulating and inserting the spacer into the disc space between the first vertebral body and the second vertebral body to provide fusion of the first vertebral body to the second vertebral body via biological bone fusion and screw fusion, the tool comprising:
an elongate shaft;
first and second gripper prongs positioned such that the first gripper prong engages the first slot of the spacer and the second gripper prong engages the second slot of the spacer when the tool engages the spacer; and
a screw guide for controlling a direction of the first screw and the second screw that are inserted into the first internal screw guide and the second internal screw guide of the spacer, wherein the screw guide is positioned between the plurality of prongs with distal ends of the prongs extending distally past the screw guide.

17. The apparatus of claim 1, and wherein the screw locking mechanism comprises titanium.

18. The apparatus of claim 1, and further comprising means for performing supplemental screw locking.

19. An intervertebral combination internal screw guide and fixation apparatus configured to be inserted into a disc space between a first vertebral body and a second vertebral body and to provide fusion of the first vertebral body to the second vertebral body via biological bone fusion and screw fusion, the apparatus comprising:
an intervertebral spacer including a top wall, a bottom wall, and first and second sidewalls, wherein the intervertebral spacer defines:
an open space between the top, bottom, first, and second sidewalls capable of receiving bone filling for biological bone fusion,
a first slot on a first outer side of the first sidewall,
a second slot on a second outer side of the second sidewall of the two sidewalls, wherein the second slot is positioned opposite of the first slot, wherein the first slot is positioned along a first centerline axis that bisects the first side wall and wherein the second slot is positioned along a second centerline axis that bisects the second side wall,
a first internal screw guide having a first entry opening and a first exit opening, the first entry opening of the first internal screw guide formed at least partially in a top surface of the top wall and the first exit opening formed at least partially in a bottom surface of the top wall and at least partially in a first side surface of the top wall,
a second internal screw guide having a second entry opening and a second exit opening, the second entry opening of the second internal screw guide formed at least partially in the top surface of the top wall and the second exit opening formed at least partially in the bottom surface of the top wall and at least partially in a second side surface of the top wall so as to extend in a direction different than that of the first internal screw guide,
an indentation in the top surface of the top wall extending between at least a portion of the first internal screw guide and the second internal screw guide, and
a hole extending into the top wall at an angle that is perpendicular to the top surface of the top wall and at a position that is located in the indentation between the first internal screw guide and the second internal screw guide,
a first screw having a first screw head and a first threaded body that is sized and configured to be inserted through the first internal screw guide;
a second screw having a second screw head and a second threaded body that is sized and configured to be inserted through the second internal screw guide; and
a screw locking mechanism positioned in the indentation of the intervertebral spacer and extending at least partially into the hole, wherein the screw locking mechanism has a central portion sized and configured to be inserted in the hole and has first and second side portions extending perpendicular to the hole so as to engage the first and second screws and secure the first and second screws in position when the first and second screws are inserted into the first and second internal screw guides.

20. An intervertebral combination internal screw guide and fixation apparatus configured to be inserted into a disc space between a first vertebral body and a second vertebral body and to provide fusion of the first vertebral body to the second vertebral body via biological bone fusion and screw fusion, the apparatus comprising:
an intervertebral spacer including a top wall, a bottom wall, and first and second sidewalls, wherein the intervertebral spacer defines:
an open space between the top, bottom, first, and second sidewalls capable of receiving bone filling for biological bone fusion,
a first slot on a first outer side of the first sidewall,
a second slot on a second outer side of the second sidewall of the two sidewalls, wherein the second slot is positioned opposite of the first slot, wherein the first slot is positioned along a first centerline axis that bisects the first side wall and wherein the second slot is positioned along a second centerline axis that bisects the second side wall,
a first internal screw guide having a first entry opening and a first exit opening, the first entry opening of the first internal screw guide formed at least partially in a top surface of the top wall and the first exit opening formed at least partially in a bottom surface of the top wall and at least partially in a first side surface of the top wall,
a second internal screw guide having a second entry opening and a second exit opening, the second entry opening of the second internal screw guide formed at least partially in the top surface of the top wall and the second exit opening formed at least partially in the bottom surface of the top wall and at least partially in a second side surface of the top wall so as to extend in a direction different than that of the first internal screw guide,
an indentation in the top surface of the top wall extending between at least a portion of the first internal screw guide and the second internal screw guide, and
a hole extending into the top wall at an angle that is perpendicular to the top surface of the top wall and at a position that is located in the indentation between the first internal screw guide and the second internal screw guide,
a first screw having a first screw head and a first threaded body that is sized and configured to be inserted through the first internal screw guide;
a second screw having a second screw head and a second threaded body that is sized and configured to be inserted through the second internal screw guide; and
a screw locking mechanism positioned in the indentation of the intervertebral spacer and extending at least partially into the hole, wherein the screw locking mechanism comprises a first curved portion extending toward the first internal screw guide in engaging contact with the first screw when the first screw is inserted in the first internal screw guide and a second curved portion extending toward the second internal screw guide in engaging contact with the second screw when the second screw is inserted in the second internal screw guide.

* * * * *